United States Patent
Langohr et al.

(10) Patent No.: US 6,667,351 B2
(45) Date of Patent: *Dec. 23, 2003

(54) ARTICLES HAVING ELEVATED TEMPERATURE ELASTICITY MADE FROM IRRADIATED AND CROSSLINKED ETHYLENE POLYMERS AND METHOD FOR MAKING THE SAME

(75) Inventors: Michael F. Langohr, Lake Jackson, TX (US); Rajen M. Patel, Lake Jackson, TX (US); Selim Bensason, Houston, TX (US); Jill M. Martin, Lake Jackson, TX (US); Thoi H. Ho, Lake Jackson, TX (US); Nancy J. Schrock, Lake Jackson, TX (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/086,057

(22) Filed: Feb. 28, 2002

(65) Prior Publication Data

US 2002/0132923 A1 Sep. 19, 2002

Related U.S. Application Data

(62) Division of application No. 09/313,740, filed on May 18, 1999, now Pat. No. 6,500,540.
(60) Provisional application No. 60/086,059, filed on May 18, 1998.

(51) Int. Cl.[7] .................................................. C08J 3/28
(52) U.S. Cl. ........................ 522/157; 522/158; 522/161; 522/160
(58) Field of Search .............................. 522/157, 158, 522/161, 160

(56) References Cited

U.S. PATENT DOCUMENTS

| 2,957,512 | A | 10/1960 | Wade et al. | 154/33.05 |
| 3,156,242 | A | 11/1964 | Crowe | 128/296 |
| 3,485,706 | A | 12/1969 | Evans | 161/72 |

(List continued on next page.)

FOREIGN PATENT DOCUMENTS

| CA | 935598 | 10/1973 | |
| EP | 0416815 A2 | 3/1991 | C08F/10/00 |
| EP | 0515203 A3 | 11/1992 | C08L/67/04 |

(List continued on next page.)

OTHER PUBLICATIONS

Dealy, John, *Rheometers for Molten Plastics*, Van Nostrand Reinhold Co., (1982) p. 97–99.
Ramanurthy, A.V., *Wall Slip in Viscous Fluids and Influence of Materials of Construction*, John Wiley & Sons, Inc., Journal of Rheology, 30(2), 1986, pp. 337–357.

(List continued on next page.)

*Primary Examiner*—Cynthia H. Kelly
*Assistant Examiner*—J. M. Gray
(74) *Attorney, Agent, or Firm*—Whyte Hirschboeck Düdek SC

(57) ABSTRACT

The present invention relates to elastic articles comprising a crosslinked or crosslinkable ethylene polymer and a method for making the same. In particular, the invention relates to a shaped article (e.g. film or fiber) characterized by improved elasticity at elevated temperatures and comprising a substantially cured, irradiated, or crosslinked (or curable, irradiated or crosslinkable) homogeneously branched ethylene polymer. The improved elastic article of the present invention is particularly suitable for use in applications where good elasticity must be maintained at elevated temperatures such as, for example, personal hygiene items and disposable infection-control garments at body temperatures of about 100° F. (38° C.).

14 Claims, 5 Drawing Sheets

U.S. PATENT DOCUMENTS

| | | | | |
|---|---|---|---|---|
| 3,520,861 | A | 7/1970 | Thomson et al. | 260/88.1 |
| 3,645,992 | A | 2/1972 | Elston | 260/80.78 |
| 3,881,489 | A | 5/1975 | Hartwell | 128/287 |
| 3,914,342 | A | 10/1975 | Mitchell | 260/897 |
| 3,989,867 | A | 11/1976 | Sisson | 428/132 |
| 4,076,698 | A | 2/1978 | Anderson et al. | 526/348.6 |
| 4,322,027 | A | 3/1982 | Reba | 226/97 |
| 4,340,563 | A | 7/1982 | Appel et al. | 264/518 |
| 4,381,781 | A | 5/1983 | Sciaraffa et al. | 604/372 |
| 4,413,110 | A | 11/1983 | Kavesh et al. | 526/348.1 |
| 4,425,393 | A | 1/1984 | Benedyk et al. | 428/95 |
| 4,500,648 | A | 2/1985 | Malpass | 502/118 |
| 4,544,762 | A | 10/1985 | Kaminsky et al. | 556/179 |
| 4,584,347 | A | 4/1986 | Harpell et al. | 525/119 |
| 4,599,392 | A | 7/1986 | McKinney et al. | 526/318.6 |
| 4,663,220 | A | 5/1987 | Wisneski et al. | 428/221 |
| 4,668,566 | A | 5/1987 | Braun | 428/286 |
| 4,798,081 | A | 1/1989 | Hazlitt et al. | 73/53 |
| 4,801,482 | A | 1/1989 | Goggans et al. | 428/68 |
| 4,861,652 | A | 8/1989 | Lippert et al. | 428/284 |
| 4,879,170 | A | 11/1989 | Radwanski et al. | 428/233 |
| 4,939,016 | A | 7/1990 | Radwanski et al. | 428/152 |
| 4,940,464 | A | 7/1990 | Van Gompel et al. | 604/396 |
| 4,957,790 | A | 9/1990 | Warren | 428/34.9 |
| 4,960,878 | A | 10/1990 | Crapo et al. | 556/179 |
| 4,981,747 | A | 1/1991 | Morman | 428/198 |
| 4,988,781 | A | 1/1991 | McKinney et al. | 526/68 |
| 5,008,204 | A | 4/1991 | Stehling | 436/85 |
| 5,015,749 | A | 5/1991 | Schmidt et al. | 556/179 |
| 5,026,798 | A | 6/1991 | Canich | 526/127 |
| 5,037,416 | A | 8/1991 | Allen et al. | 604/385.1 |
| 5,041,583 | A | 8/1991 | Sangokoya | 556/179 |
| 5,041,584 | A | 8/1991 | Crapo et al. | 556/179 |
| 5,041,585 | A | 8/1991 | Deavenport et al. | 556/179 |
| 5,055,438 | A | 10/1991 | Canich | 502/117 |
| 5,064,802 | A | 11/1991 | Stevens et al. | 502/155 |
| 5,085,654 | A | 2/1992 | Buell | 604/370 |
| 5,086,024 | A | 2/1992 | Crapo et al. | 502/117 |
| 5,089,321 | A | 2/1992 | Chum et al. | 428/218 |
| 5,108,820 | A | 4/1992 | Kaneko et al. | 428/198 |
| 5,132,380 | A | 7/1992 | Stevens et al. | 526/126 |
| 5,189,192 | A | 2/1993 | LaPointe et al. | 556/179 |
| 5,196,000 | A | 3/1993 | Clear et al. | 604/385.2 |
| 5,218,071 | A | 6/1993 | Tsutsui et al. | 526/348 |
| 5,272,236 | A | 12/1993 | Lai et al. | 526/348.5 |
| 5,278,272 | A | 1/1994 | Lai et al. | 526/348.5 |
| 5,292,845 | A | 3/1994 | Kawasaki et al. | 526/336 |
| 5,322,728 | A | 6/1994 | Davey et al. | 428/296 |
| 5,324,576 | A | 6/1994 | Reed et al. | 428/224 |
| 5,336,552 | A | 8/1994 | Strack et al. | 428/224 |
| 5,374,696 | A | 12/1994 | Rosen et al. | 526/126 |
| 5,382,400 | A | 1/1995 | Pike et al. | 264/168 |
| 5,384,373 | A | 1/1995 | McKinney et al. | 526/212 |
| 5,453,410 | A | 9/1995 | Kolthammer et al. | 502/155 |
| 5,470,993 | A | 11/1995 | Devore et al. | 556/11 |
| 5,472,775 | A | 12/1995 | Obijeski et al. | 428/220 |
| 5,494,874 | A | 2/1996 | Rosen et al. | 502/155 |
| 5,525,257 | A | 6/1996 | Kleinstuck et al. | 252/181 |
| 5,532,394 | A | 7/1996 | Rosen et al. | 556/11 |
| 5,665,800 | A | 9/1997 | Lai et al. | 524/115 |
| 5,824,718 | A * | 10/1998 | Penfold et al. | 522/120 |
| 6,176,952 | B1 | 1/2001 | Maugans et al. | 156/73.1 |
| 6,384,139 | B1 * | 5/2002 | Ho et al. | 525/123 |
| 6,437,014 | B1 * | 8/2002 | Ho et al. | 522/75 |
| 6,500,540 | B1 * | 12/2002 | Langohr et al. | 428/364 |
| 2002/0049269 | A1 * | 4/2002 | Ho et al. | 524/186 |
| 2002/0061945 | A1 * | 5/2002 | Oates et al. | 524/167 |
| 2002/0132923 | A1 * | 9/2002 | Langohr et al. | 525/191 |
| 2002/0151609 | A1 * | 10/2002 | Cjaidjaru et al. | 522/60 |

FOREIGN PATENT DOCUMENTS

| | | | |
|---|---|---|---|
| EP | 0520732 B1 | 12/1992 | C08F/10/00 |
| EP | 0748846 A3 | 2/1997 | C08L/67/04 |
| WO | 90/01521 | 2/1990 | C08L/67/04 |
| WO | 93/07187 | 4/1993 | C08F/10/02 |
| WO | 93/07188 | 4/1993 | C08F/10/02 |
| WO | 93/07189 | 4/1993 | C08F/10/02 |
| WO | 93/08199 | 4/1993 | C07F/7/28 |
| WO | 93/08221 | 4/1993 | C08F/10/00 |
| WO | 94/25515 | 11/1994 | C08J/9/14 |
| WO | 94/25647 | 11/1994 | D01F/6/30 |
| WO | 95/29197 | 11/1995 | C08F/255/02 |
| WO | 97/26297 | 7/1997 | C08L/23/16 |
| WO | 98/26001 | 6/1998 | C08L/51/05 |
| WO | 99/10395 | 3/1999 | C08F/210/00 |

OTHER PUBLICATIONS

Randall, James C., *A Review of High Resolution Liquid $^{13}$Carbon Nuclear Magnetic Resonance Characterizations of Ethylene–Based Polymers*, JMS–Rev. Macromol. Chem. Phys., C29(2&3), 1989, pp. 201–317.

Randall, James C., *A Review of High Resolution Liquid $^{13}$Carbon Nuclear Magnetic Resonance Characterizations of Ethylene–Based Polymers*, Rev. Macromol. Chem. Phys., C29(2&3), 1989, pp. 285–297.

Rudin, Alfred, *Measurement of Long–Chain Branch Frequency in Synthetic Polymers*, John Wiley & Sons, Inc., Modern Methods of Polymer Characterization, 1991, pp. 103–112.

Shida, M., et al., *Correlation of Low Density Polyethylene Rheological Measurements with Optical and Processing Properties*, Polymer Engineering and Science, Nov., 1977, vol. 17, No. 11, pp. 769–774.

Wild, L., et al., *Determination of Branching Distributions in Polyethylene and Ethylene Copolymers*, John Wiley & Sons, Inc., Journal of Polymer Science: Polymer Physics Edition, vol. 20, 1982, pp. 441–455.

Zimm, Bruno H., et al., *The Dimensions of Chain Molecules Containing Branches and Rings*, The Journal of Chemical Physics, vol. 17, No. 12, Dec., 1949, pp. 1301–1314.

* cited by examiner

Data obtained using the 5-cycle test

ARTICLES HAVING ELEVATED TEMPERATURE ELASTICITY MADE FROM IRRADIATED AND CROSSLINKED ETHYLENE POLYMERS AND METHOD FOR MAKING THE SAME

CROSS-REFERENCE TO RELATED APPLICATION

This application is a division of U.S. patent application Ser. No. 09/313,740, filed May 18, 1999 now U.S. Pat. No. 6,500,540; which claims priority benefit of U.S. Provisional Application Serial No. 60/086,059, filed May 18, 1998, expired.

CROSS-REFERENCE TO RELATED APPLICATION

This application claims the priority benefit of provisional application No. 60/086059, field May 18, 1998, the disclosure of which is incorporated herein by reference in its entirety.

FIELD OF THE INVENTION

The present invention relates to a crosslinked, heat resistant elastic article having elevated temperature elasticity comprising a cured, irradiated or crosslinked ethylene polymer and a method for making a crosslinked, heat resistant elastic article. In particular, the invention relates to a shaped article (e.g. film or fiber) characterized by heat resistance and improved elasticity at elevated temperatures and comprising a substantially cured, irradiated, or crosslinked homogeneously branched ethylene polymer. The improved elastic article of the present invention is particularly suitable for use in applications where good elasticity must be maintained at elevated temperatures such as, for example, personal hygiene items and disposable infection-control garments at body temperatures of about 100° F. (38° C.).

BACKGROUND OF THE INVENTION

Materials with excellent stretchability and elasticity are needed to manufacture a variety of disposal and durable articles such as, for example, incontinence pads, disposable diapers, training pants, sport apparel and furniture upholstery. Stretchability and elasticity are performance attributes which function to effectuate a closely conforming fit to the body of the wearer or to the frame of the item. It is desirable to maintain the conforming fit during repeated use, extensions and retractions at body temperatures. Further, for incontinence articles, stretchability and elasticity are particularly desirable to ensure comfort and provide security against unwanted leaks.

Disposable articles are typically elastic composite materials prepared from a combination of polymer film, fibers, sheets and absorbent materials as well as a combination of fabrication technologies. Whereas the fibers are prepared by well known processes such as spun bonding, melt blowing, melt spinning and continuous filament wounding techniques, the film and sheet forming processes typically involve known extrusion and coextrusion techniques, e.g., blown film, cast film, profile extrusion, injection molding, extrusion coating, and extrusion sheeting.

A material is typically characterized as elastic where it has a high percent elastic recovery (i.e., a low percent permanent set) after application of a biasing force. Ideally, elastic materials are characterized by a combination of three important properties, i.e., a low percent permanent set, a low stress or load at strain, and a low percent stress or load relaxation. That is, there should be (1) a low stress or load requirement to stretch the material, (2) no or low relaxing of the stress or unloading once the material is stretched, and (3) complete or high recovery to original dimensions after the stretching, biasing or straining is discontinued.

Lycra (spandex) is a segmented polyurethane elastic material which is known to exhibit good elastic properties. But Lycra tends to be extremely cost prohibitive for a many of applications. Also, Lycra like natural rubbers tend to exhibit poor environmental resistance to ozone, chlorine and high temperature, especially in the presence of moisture.

Natural rubbers, as discussed by Ferdinand Rodriguez in *Principles of Polymer Systems*, pp. 242–43, McGraw-Hill (1982), the disclosure of which is incorporated herein by reference, generally show decreases in elongation to break with increase in degree of crosslinking. Furthermore, at high degrees of crosslinking, even tenacity at break may decrease for natural rubbers.

Elastic materials such as films, strips, coating, ribbons and sheet comprising at least one substantially linear ethylene polymer are disclosed in U.S. Pat. No. 5,472,775 to Obijeski et al., the disclosure of which is incorporated herein by reference. But U.S. Pat. No. 5,472,775 does not disclose the performance of these materials at elevated temperatures (i.e., at temperatures above room temperature).

WO 94/25647 (Knight et al.), the disclosure of which is incorporated herein by reference, discloses elastic fibers and fabrics made from homogeneously branched substantially linear ethylene polymers. The fibers are said to posses at least 50 percent recovery (i.e., less than or equal 50% permanent set) at 100 percent strain. But there is no disclosure in WO 94/25647 regarding the elasticity of these fibers at elevated temperatures, nor is there any disclosure regarding resistance to high temperatures.

U.S. Pat. No. 5,322,728 to Davey et al., the disclosure of which is incorporated herein by reference, discloses elastic fibers comprised of single site catalyzed ethylene polymers. But polymers are not cured, irradiated or crosslinked and therefore are believed to exhibit poor elevated temperature elasticity.

WO 95/29197 (Penfold et al.), the disclosure of which is incorporated herein by reference, discloses curable, silane-grafted substantially ethylene polymers which are useful for use in wire and cable coatings, weather-stripping and fibers. WO 95/29197 reports examples which include fibers comprising silane-grafted substantially ethylene polymers having densities of 0.868 g/cm$^3$ and 0.870 g/cm$^3$. While example fibers are shown to exhibit improved elastic recovery at elevated temperatures, there is no disclosure regarding percent stress or load relaxation performance at elevated temperatures.

U.S. Pat. No. 5,324,576 to Reed et al., the disclosure of which is incorporated herein by reference, discloses an elastic nonwoven web of microfibers of radiation crosslinked ethylene/alpha olefin copolymers, preferably having a density less than 0.9 g/cm$^3$. The examples reported in U.S. Pat. No. 5,324,576 comprise ethylene polymers having polymer densities greater than or equal to 0.871 g/cm$^3$ which subjected to electron beam radiation. But Reed et al. provide no disclosure regarding the elastic performance of these radiated polymers at elevated temperatures.

U.S. Pat. No. 5,525,257 to Kurtz et al., the disclosure of which is incorporated herein by reference, discloses that low levels of irradiation of less than 2 megarads of Ziegler catalyzed linear low density ethylene polymer results in improved stretchability and bubble stability without measurable gelation.

U.S. Pat. No. 4,425,393 to Benedyk et al., the disclosure of which is incorporated herein by reference, discloses low modulus fibers having diameters in the range of 0.5 to 3 mils (about 1 to about 37 denier).

Canadian Patent No. 935,598 to Hardy et al., the disclosure of which is incorporated herein by reference, discloses elastic fibers comprised of various ethylene polymers wherein the fibers are post-drawn (stretched) and crosslinked while under tension.

U.S. Pat. No. 4,957,790 to Warren, the disclosure of which is incorporated herein by reference, discloses the use of pro-rad compounds and irradiation to prepare heat-shrinkable linear low density polyethylene films having an increased orientation rate during fabrication. In the examples provided therein, Warren employs Ziegler catalyzed ethylene polymers having densities greater than or equal to 0.905 g/cm$^3$.

In spite of various disclosures relating to elastic ethylene polymer articles, including articles comprising curable, radiated and/or crosslinked ethylene polymers, there is a present need for cost-effective elastic articles having good heat resistance and elasticity at elevated temperatures, especially at human body temperatures of about 100° F. There is also a need for a method of making elastic articles having good elasticity at elevated temperatures. We have discovered that these and other objects can be completely met by the invention herein described.

SUMMARY OF THE INVENTION

We have discovered that elastic articles comprising a substantially cured, radiated or crosslinked ethylene polymer wherein the polymer is characterized as having a polymer density of less than 0.89 g/cm$^3$, especially less than 0.87 g/cm$^3$ and most especially less than or equal to 0.865 g/cm$^3$ (or a differential scanning calorimetry (DSC) crystallinity at 23° C. of less than 26 weight percent, especially 12 weight percent, and most especially less than or equal to 8.5 weight percent). These novel articles exhibit excellent elasticity at room temperature and at elevated temperatures.

The broad aspect of the invention provides a heat resistant, shaped cured, irradiated or crosslinked article comprising an ethylene interpolymer of ethylene interpolymerized with at least one other monomer and characterized as having:

a) a polymer density of less than 0.89 g/cm$^3$ or a DSC crystallinity at 23° C., as determined using differential scanning calorimetry, of less than 26 weight percent before being shaped, cured, irradiated or crosslinked and b) in meltspun fiber form, a value less than 0.75 for the expression $$Abs[\Delta E/E_0]+Abs[\Delta T/T_0]$$

where ΔE and ΔT are taken from a stress-strain plot, as determined using an Instron tensiometer at 500 mm/minute crosshead speed and 10.2 cm gage length and from the average of four replications of five fiber samples; ΔE is taken as the difference in percent elongation between the cured, irradiated or crosslinked polymer and the uncured, irradiated or uncrosslinked interpolymer at a tenacity of 0.4 grams/denier; $E_0$ is taken as the percent elongation of the uncured, irradiated or uncrosslinked interpolymer at a tenacity of 0.4 grams/denier; ΔT is taken as the difference in tenacity (in grams/denier) between the cured, irradiated or crosslinked polymer and the uncured, irradiated or uncrosslinked polymer at a percent elongation of 300 percent; $T_0$ is taken as the tenacity (in grams/denier) of the uncured, irradiated or uncrosslinked interpolymer at a percent elongation of 300 percent; and Abs denotes absolute value.

Another aspect of the invention is a heat resistant cured, irradiated or crosslinked elastic fiber comprising ethylene interpolymerized with at least one other monomer wherein the interpolymer is characterized as having:

a) polymer density of less than 0.89 g/cm$^3$ or a crystallinity at 23° C., as determined using differential scanning calorimetry, of less than 26 weight percent before being shaped, cured, irradiated or crosslinked and b) in meltspun fiber form, a value less than 0.75 for the expression $$Abs[\Delta E/E_0]+Abs[\Delta T/T_0]$$

where ΔE and ΔT are taken from a stress-strain plot, as determined using an Instron tensiometer at 500 mm/minute crosshead speed and 10.2 cm gage length and from the average of four replications of five fiber samples; ΔE is taken as the difference in percent elongation between the cured, irradiated or crosslinked polymer and the uncured, irradiated or uncrosslinked interpolymer at a tenacity of 0.4 grams/denier; $E_0$ is taken as the percent elongation of the uncured, irradiated or uncrosslinked interpolymer at a tenacity of 0.4 grams/denier; ΔT is taken as the difference in tenacity (in grams/denier) between the cured, irradiated or crosslinked polymer and the uncured, irradiated or uncrosslinked polymer at a percent elongation of 300 percent; $T_0$ is taken as the tenacity (in grams/denier) of the uncured, irradiated or uncrosslinked interpolymer at a percent elongation of 300 percent; and Abs denotes absolute value.

A third aspect of the invention is a heat resistant shaped elastic article which comprises at least one ethylene interpolymer which has been cured, irradiated or crosslinked wherein the interpolymer comprises ethylene interpolymerized with at least one other monomer and is characterized as having:

(a) a polymer density of less than 0.87 g/cm$^3$ before being shaped, cured, irradiated or crosslinked, (b) a percent permanent set of less than or equal 25 at 23° C. and 200 percent strain when measured at a 2 mil thickness using an Instron tensiometer after being shaped, cured, irradiated or crosslinked, (c) a percent stress relaxation of less than or equal 25 at 23° C. and 200 percent strain when measured at a 2 mil thickness using a Instron tensiometer after being shaped, cured, irradiated or crosslinked, and (d) a percent stress relaxation of less than or equal 55 at 38° C. and 200 percent strain when measured at a 2 mil thickness using an Instron tensiometer after.

A fourth aspect of the invention is a method of making an elastic article comprising the steps of (a) providing an ethylene interpolymer having a density of less than 0.87 g/cm$^3$, (b) fabricating the article from the interpolymer, and (c) after the fabrication, subjecting the article to heat or ionizing radiation or both.

A fifth aspect of the invention is a method of making an elastic article comprising the steps of (a) providing an ethylene interpolymer having a density of less than 0.87 g/cm$^3$, (b) incorporating a pro-rad crosslink additive into the interpolymer, (c) fabricating the article from the interpolymer, and (d) after fabrication, subjecting the article to heat or ionizing radiation or both.

Preferably, the article is fabricated using an extrusion technique (i.e., the method consists of melting the interpolymer). Suitable extrusion techniques include, but are not limited to, fiber melt spinning, fiber melt blowing, film blowing, cast filed, injection molding, or rotomolding technique. Preferably, the extrudate, filament, web or part is permitted to cool or is quenched to ambient temperature (i.e., permitted to substantially solidify) before the application of additional heating or ionizing radiation.

In a preferred embodiment of the invention, the ethylene polymer is a homogeneously branched ethylene polymer, especially a substantially linear ethylene polymer. In another preferred embodiment, the ionizing radiation is provided by electron beam irradiation.

We discovered that (unlike natural rubbers) curing, irradiation or crosslinking (increased crosslink densities) do not decrease the elongation at break or tenacity at break for homogeneously branched ethylene polymers having a polymer density of less than 0.89 g/cm$^3$ and that articles (especially fibers) of cured, irradiated or crosslinked homogeneously branched ethylene polymers exhibit substantially improve heat resistance.

We also discovered that there is a subset of ethylene polymers which provide completely unexpected elastic performance results when cured, radiated or crosslinked. In particular, we found for the broad range of polymer densities above and below 0.87 g/cm$^3$, curing, radiation or crosslinking dramatically decrease percent permanent set performance (i.e., improve elasticity or elastic recovery) and have no substantial effect on ambient percent stress or load relaxation performance. But while tending to adversely affect (i.e., increase) or have no effect on percent stress or load relaxation at elevated temperatures for polymer having densities equal to or greater than 0.865 g/cm$^3$, surprisingly curing, radiation and crosslinking decreases (i.e., improves) the elevated temperature percent stress or load relaxation performance of ethylene interpolymer having a polymer density less than 0.87 g/cm$^3$ or a DSC crystallinity at 23° C. less than 12 weight percent. That is, curing, radiating or crosslinking is an effective means for providing elastic materials and articles characterized as having excellent elevated temperature stress relaxation characteristics.

Not only is the dramatically different response to irradiation or crosslinking surprisingly in itself, these results are surprising for other reasons as well. For example, these results are surprising and unexpected because at a density of 0.87 g/cm$^3$, ethylene polymers are already substantially amorphous. That is, a cross-over or transition in elastic performance attributable to curing, radiation or crosslinking would ordinarily be expected to relate to the amorphosity of the polymer; but according to hexane extraction data at 50° C., determined according to the Food and Drug Administration (FDA) test method set forth under 21 37 C.F.R. §§177.1520 (d)(3)(ii), ethylene polymers are substantially amorphous at a density of 0.89 g/cm$^3$ and below. Given such small differences in amorphosity or crystallinity, dramatic elasticity differences in response to irradiation or crosslinking simply would not ordinarily be expected.

Accordingly, the shaped elastic articles of present invention exhibit a unique combination of properties such as tenacity at break, elongation, elastic recovery, chlorine and aromatic/polar solvent resistance, moisture resistance, heat aging and excellent high temperature mechanical performance compared to traditional elastic materials, for example, natural rubber and spandex.

DETAILED DESCRIPTION OF THE INVENTION

Figure 1:
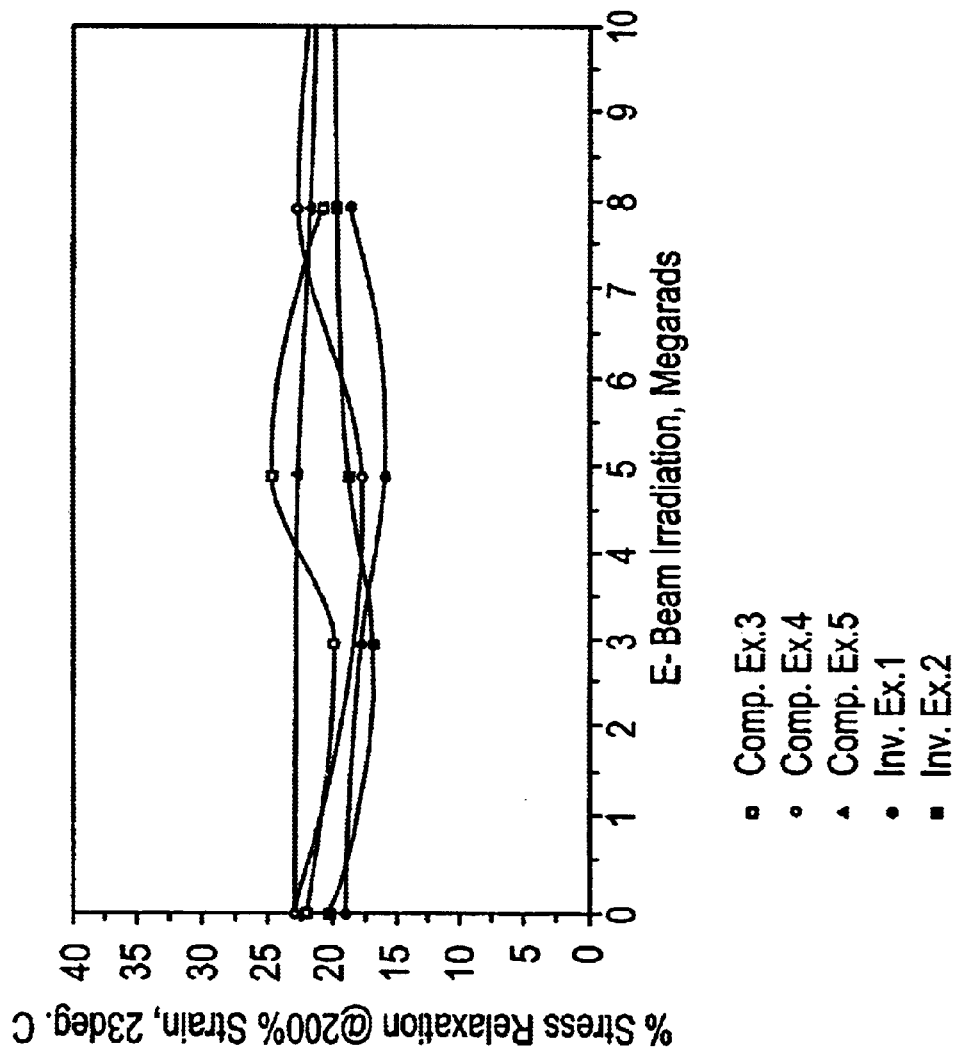
FIG. 1 is a plot of percent stress relaxation at 23° C. versus megarads of electron beam radiation for Inventive Examples 1 and 2 and comparative runs 3, 4 and 5.

The term "elastic" as used herein refers to a material having a permanent set less than 60 percent, especially less than or equal to 25 percent (i.e. especially greater than or equal to 87.5 percent recovery) at 200 percent strain and is stretchable to a stretched, biased length at least 150 percent greater than its relaxed, unstretched length. Elastic materials are also referred to in the art as "elastomers" and "elastomeric".

The term "nonelastic" as used herein means the material or article is not elastic as defined herein (i.e. the martial or article has a percent permanent set greater than Elastic materials and articles include, the cured, radiated or crosslinked article, ethylene interpolymer itself or both as well as, but not limited to, a fiber, film, strip, tape, ribbon, sheet, coating, molding and the like comprised of the cured, radiated or crosslinked ethylene interpolymer. Preferred elastic articles are fiber and The term "radiated" or "irradiated" as used herein means the ethylene polymer, the shaped ethylene interpolymer or the article comprised of the ethylene polymer was subjected to at least 3 megarads (or the equivalent thereof) of radiation dose whether or not there was a measurable decrease in percent xylene extractables (i.e., increase in insoluble gel). That is, substantial crosslinking may not result from the irradiation.

The terms "crosslinked" and "substantially crosslinked" as used herein mean the ethylene polymer, the shaped ethylene interpolymer or the article comprised of the ethylene polymer is characterized as having xylene extractables of less than or equal to 70 weight percent (that is, greater than or equal to 30 weight percent gel content), preferably greater than or equal to 40 weight percent (that is, greater than or equal to 60 weight percent gel content), where xylene extractables (and gel content) are determined in accordance with ASTM D-2765.

The terms "cured" and "substantially cured" as used herein means the ethylene interpolymer, the shaped ethylene interpolymer or the article comprised of the ethylene interpolymer was subjected or exposed to a treatment which induced crosslinking. As used herein, the terms relate to ethylene interpolymers comprising a grafted silane.

The terms "curable" and "crosslinkable" as used herein mean the ethylene interpolymer, the shaped ethylene interpolymer or the article comprised of the ethylene interpolymer is not crosslinked and has not been subjected or exposed to treatment which induces crosslinking although the ethylene interpolymer, the shaped ethylene interpolymer or the article comprised of the ethylene interpolymer comprises additive(s) or functionality which will effectuate crosslinking upon subjection or exposure to such treatment.

In the practice of the present invention, curing, irradiation or crosslinking can be accomplished by any means known in the art, including, but not limited to, electron-beam irradiation, beta irradiation, gamma irradiation, corona irradiation, peroxides, allyl compounds and UV radiation with or without crosslinking catalyst. Electron-beam irradiation is preferred.

Suitable electron-beam irradiation equipment is available from Energy Services, Inc. Wilmington, Mass. with capabilities of at least 100 KeV and at least 5 Kw.

The term "pro-rad additive" as used herein means a compound which is not activated during normal fabrication or processing of the ethylene interpolymer, however can be activated by the application of temperatures (heat) substantial above normal fabrication or processing temperatures or ionizing energy (or both) to effectuate some measurable gelation or preferably, substantial crosslinking.

The term "homofil" as used herein refers to fiber which has a single polymer region or domain and does not have any other distinct polymer regions (as do bicomponent fibers).

The term "meltblown" is used herein in the conventional sense to refer to fibers formed by extruding a molten thermoplastic polymer composition through a plurality of fine, usually circular, die capillaries as molten threads or filaments into converging high velocity gas streams (e.g. air) which function to attenuate the threads or filaments to reduced diameters. Thereafter, the filaments or threads are carried by the high velocity gas streams and deposited on a collecting surface to form a web of randomly dispersed meltblown fibers with average diameters generally smaller than 10 microns.

The term "spunbond" is used herein in the conventional sense to refer to fibers formed by extruding a molten thermoplastic polymer composition as filaments through a plurality of fine, usually circular, die capillaries of a spinneret with the diameter of the extruded filaments then being rapidly reduced and thereafter depositing the filaments onto a collecting surface to form a web of randomly dispersed spunbond fibers with average diameters generally between about 7 and about 30 microns.

The term "nonwoven" as used herein and in the conventional sense means a web or fabric having a structure of individual fibers or threads which are randomly interlaid, but not in an identifiable manner as is the case for a knitted fabric. The elastic fiber of the present invention can be employed to prepare nonwoven fabrics as well as composition structures comprises elastic nonwoven fabric in combination with nonelastic materials.

The term "conjugated" refers to fibers which have been formed from at least two polymers extruded from separate extruders but meltblown or spun together to form one fiber. Conjugated fibers are sometimes referred to in the art as muticomponent or bicomponent fibers. The polymers are usually different from each other although conjugated fibers may be monocomponent fibers. The polymers are arranged in substantially constantly positioned distinct zones across the cross-section of the conjugated fibers and extend continuously along the length of the conjugated fibers. The configuration of conjugated fibers can be, for example, a sheath/core arrangement (wherein one polymer is surrounded by another), a side by side arrangement, a pie arrangement or an "islands-in-the sea" arrangement. Conjugated fibers are described in U.S. Pat. No. 5,108,820 to Kaneko et al.; U.S. Pat. No. 5,336,552 to Strack et al.; and U.S. Pat. No. 5,382,400 to Pike et al., the disclosures of all of which are incorporated herein by reference. The elastic fiber of the present invention can be in a conjugated configuration, for example, as a core or sheath, or both.

The ethylene interpolymer to be irradiated, cured or crosslinked has a density at 23° C. less than 0.89 g/cm$^3$, preferably less than 0.87 g/cm$^3$, more preferably less than or equal to 0.865 g/cm$^3$, especially in the range of about 0.865 g/cm$^3$ to about 0.355 g/cm$^3$, as measured in accordance with ASTM D792. At densities higher than 0.839 g/cm$^3$ the desired improved high temperature elastic performance (especially, low percent stress or load relaxation) is not obtained. Densities less than about 0.855 g/cm$^3$ are not preferred due to their low tenacity, very low melting point and pre-crosslink handing problems (blocking and tackiness).

Preferably, the ethylene interpolymer is characterized as having a DSC crystallinity of less than 26 weight percent, preferably less than 12 weight percent, more preferably less than or equal to 8.5 weight percent, and most preferably less than or equal 6 percent.

Preferably, the ethylene interpolymer is characterized as having a melt index ($I_2$) less than 50, more preferably less than 10 g/10 minutes, as determined in accordance with ASTM D-1238, Condition 190° C./2.16 kilogram (kg).

In meltspun fiber form, the irradiated, cured or crosslinked ethylene polymer of the present invention generally has a value less than 0.75, preferably less than 0.6, more preferably less than 0.5 for the expression:

$$Abs[\Delta E/E_0]+Abs[\Delta T/T_0]$$

The irradiated, cured or crosslinked ethylene polymer of the present invention (and articles made therefrom) is characterized as having a percent permanent set of less than 60 at 23° C., preferably less than or equal 25 at 23° C., more preferably less than or equal to 20 and most preferably less than or equal to 15 at 23° C. and 38° C. and 200 percent strain when measured at a 2 mil thickness using an Instron tensiometer; or preferably a percent set elongation of less than or equal to 25, more preferably 20, most preferably 15 at 23° C. and 100 percent strain.

The irradiated, cured or crosslinked ethylene polymer of the present invention (and articles made therefrom) is characterized as having a percent stress relaxation of less than or equal 25 at 23° C. and 200 percent strain and less than or equal to 55, preferably less than or equal to 50, more preferably less than or equal to 30, most preferably less than or equal to 20 at 38° C. and 200 percent strain when measured at a 2 mil thickness using a Instron tensiometer.

Irradiation may be accomplished by the use of high energy, ionizing electrons, ultra violet rays, X-rays, gamma rays, beta particles and the like and combination thereof. Preferably, electrons are employed up to 70 megarads dosages. The irradiation source can be any electron beam generator operating in a range of about 150 kilovolts to about 6 megavolts with a power output capable of supplying the desired dosage. The voltage can be adjusted to appropriate levels which may be, for example, 100,000, 300,000, 1,000,000 or 2,000,000 or 3,000,000 or 6,000,000 or higher or lower. Many other apparati for irradiating polymeric materials are known in the art. The irradiation is usually carried out at a dosage between about 3 megarads to about 35 megarads, preferably between about 8 to about 20 megarads. Further, the irradiation can be carried out conveniently at room temperature, although higher and lower temperatures, for example 0° C. to about 60° C., may also be employed. Preferably, the irradiation is carried out after shaping or fabrication of the article. Also, in a preferred embodiment, the ethylene interpolymer which has been incorporated with a pro-rad additive is irradiated with electron beam radiation at about 8 to about 20 megarads.

Crosslinking can be promoted with a crosslinking catalyst, and any catalyst that will provide this function can be used. Suitable catalysts generally include organic bases, carboxylic acids, and organometallic compounds including organic titanates and complexes or carboxylates of lead, cobalt, iron, nickel, zinc and tin. Dibutyltindilaurate, dioctyltinmaleate, dibutyltindiacetate, dibutyltindioctoate, stannous acetate, stannous octoate, lead naphthenate, zinc caprylate, cobalt naphthenate; and the like. Tin carboxylate, especially dibutyltindilaurate and dioctyltinmaleate, are particularly effective for this invention. The catalyst (or mixture of catalysts) is present in a catalytic amount, typically between about 0.015 and about 0.035 phr.

Representative pro-rad additives include, but are not limited to, azo compounds, organic peroxides and polyfunctional vinyl or allyl compounds such as, for example, triallyl cyanurate, triallyl isocyanurate, pentaerthritol tetramethacrylate, glutaraldehyde, ethylene glycol dimethacrylate, diallyl maleate, dipropargyl maleate, dipropargyl monoallyl cyanurate, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, tert-butyl peracetate, azobisisobutyl nitrite and the like and combination thereof. Preferred pro-rad additives for use in the present invention are compounds which have poly-functional (i.e. at least two) moieties such as C=C, C=N or C=O.

At least one pro-rad additive can be introduced to the ethylene interpolymer by any method known in the art. However, preferably the pro-rad additive(s) is introduced via a masterbatch concentrate comprising the same or different base resin as the ethylene interpolymer. Preferably, the pro-rad additive concentration for the masterbatch is relatively high e.g., about 25 weight percent (based on the total weight of the concentrate).

The at least one pro-rad additive is introduced to the ethylene polymer in any effective amount. Preferably, the at least one pro-rad additive introduction amount is from about 0.001 to about 5 weight percent, more preferably from about 0.005 to about 2.5 weight percent and most preferably from about 0.015 to about 1 weight percent (based on the total weight of the ethylene interpolymer.

The term "polymer", as used herein, refers to a polymeric compound prepared by polymerizing monomers, whether of the same or a different type. As used herein, generic term "polymer" embraces the terms "homopolymer," "copolymer," "terpolymer" as well as "interpolymer."

The term "interpolymer", as used herein refers to polymers prepared by the polymerization of at least two different types of monomers. As used herein the generic term "interpolymer" includes the term "copolymers" (which is usually employed to refer to polymers prepared from two different monomers) as well as the term "terpolymers" (which is usually employed to refer to polymers prepared from three different types of monomers).

The term "homogeneously branched ethylene polymer" is used herein in the conventional sense to refer to an ethylene interpolymer in which the comonomer is randomly distributed within a given polymer molecule and wherein substantially all of the polymer molecules have the same ethylene to comonomer molar ratio. The term refers to an ethylene interpolymer that are manufactured using so-called homogeneous or single-site catalyst systems known in the art such Ziegler vanadium, hafnium and zirconium catalyst systems and metallocene catalyst systems e.g., a constrained geometry catalyst systems which is further described herein below.

Homogeneously branched ethylene polymers for use in the present invention can be also described as having less than 15 weight percent, preferably less 10 weight percent, more preferably less than 5 and most preferably zero (0) weight percent of the polymer with a degree of short chain branching less than or equal to 10 methyls/1000 carbons. That is, the polymer contains no measurable high density polymer fraction (e.g., there is no fraction having a density of equal to or greater than 0.94 g/cm$^3$), as determined, for example, using a temperature rising elution fractionation (TREF) technique and infrared or 13C nuclear magnetic resonance (NMR) analysis.

Preferably, the homogeneously branched ethylene polymer is characterized as having a narrow, essentially single melting TREF profile/curve and essentially lacking a measurable high density polymer portion, as determined using a temperature rising elution fractionation technique (abbreviated herein as "TREF").

The composition distribution of an ethylene interpolymer can be readily determined from TREF as described, for example, by Wild et al., *Journal of Polymer Science, Poly. Phys. Ed.*, Vol. 20, p. 441 (1982), or in U.S. Pat. Nos. 4,798,081; 5,008,204; or by L. D. Cady, "The Role of Comonomer Type and Distribution in LLDPE Product Performance," SPE Regional Technical Conference, Quaker Square Hilton, Akron, Ohio, October 1–2, pp. 107–119 (1985), the disclosures of all which are incorporated herein by reference.

The composition (monomer) distribution of the interpolymer can also be determined using $^{13}$C NMR analysis in accordance with techniques described in U.S. Pat. Nos. 5,292,845; 4,798,081; 5,089,321 and by J. C. Randall, *Rev. Macromol. Chem. Phys.*, C29, pp. 201–317 (1989), the disclosures of all of which are incorporated herein by reference.

In analytical temperature rising elution fractionation analysis (as described in U.S. Pat. No. 4,798,081 and abbreviated herein as "ATREF"), the film or composition to be analyzed is dissolved in a suitable hot solvent (e.g., trichlorobenzene) and allowed to crystallized in a column containing an inert support (stainless steel shot) by slowly reducing the temperature. The column is equipped with both a refractive index detector and a differential viscometer (DV) detector. An ATREF-DV chromatogram curve is then generated by eluting the crystallized polymer sample from the column by slowly increasing the temperature of the eluting solvent (trichlorobenzene). The ATREF curve is also frequently called the short chain branching distribution (SCBD) or composition distribution (CD) curve, since it indicates how evenly the comonomer (e.g., octene) is distributed throughout the sample in that as elution temperature decreases, comonomer content increases. The refractive index detector provides the short chain distribution information and the differential viscometer detector provides an estimate of the viscosity average molecular weight. The composition distribution and other compositional information can also be determined using crystallization analysis fractionation such as the CRYSTAF fractionalysis package available commercially from PolymerChar, Valencia, Spain.

Preferred homogeneously branched ethylene polymers (such as, but not limited to, substantially linear ethylene polymers) have a single melting peak between −30 and 150° C., as determined using differential scanning calorimetry (DSC), as opposed to traditional Ziegler polymerized heterogeneously branched ethylene polymers (e.g., LLDPE and ULDPE or VLDPE) which have two or more melting points.

The single melting peak is determined using a differential scanning calorimeter standardized with indium and deionized water. The method involves about 5–7 mg sample sizes, a "first heat" to about 180° C. which is held for 4 minutes, a cool down at 10° C./min. to −30° C. which is held for 3 minutes, and heat up at 10° C./min. to 150° C. to provide a "second heat" heat flow vs. temperature curve from which the melting peak(s) is obtained. Total heat of fusion of the polymer is calculated from the area under the curve.

The homogeneously branched ethylene polymers for use in the invention can be either a substantially linear ethylene polymer or a homogeneously branched linear ethylene polymer.

The term "linear" as used herein means that the ethylene polymer does not have long chain branching. That is, the polymer chains comprising the bulk linear ethylene polymer have an absence of long chain branching, as in the case of traditional linear low density polyethylene polymers or linear high density polyethylene polymers made using Ziegler polymerization processes (e.g., U.S. Pat. No. 4,076,698 (Anderson et al.)), sometimes called heterogeneous polymers. The term "linear" does not refer to bulk high pressure branched polyethylene, ethylene/vinyl acetate copolymers, or ethylene/vinyl alcohol copolymers which are known to those skilled in the art to have numerous long chain branches.

The term "homogeneously branched linear ethylene polymer" refers to polymers having a narrow short chain branching distribution and an absence of long chain branching. Such "linear" uniformly branched or homogeneous polymers include those made as described in U.S. Pat. No. 3,645,992 (Elston) and those made using so-called single site catalysts in a batch reactor having relatively high ethylene concentrations (as described in U.S. Pat. No. 5,026,798 (Canich) or in U.S. Pat. No. 5,055,438 (Canich)) or those made using constrained geometry catalysts in a batch reactor also having relatively high olefin concentrations (as described in U.S. Pat. No. 5,064,802 (Stevens et al.) or in EP 0 416 815 A2 (Stevens et al.)).

Typically, homogeneously branched linear ethylene polymers are ethylene/α-olefin interpolymers, wherein the α-olefin is at least one $C_3$–$C_{20}$ α-olefin (e.g., propylene, 1-butene, 1-pentene, 4-methyl-1-pentene, 1-hexene, 1-octene and the like) and preferably the at least one $C_3$–$C_{20}$ α-olefin is 1-butene, 1-hexene or 1-octene. Most preferably, the ethylene/α-olefin interpolymer is a copolymer of ethylene and a $C_3$–$C_{20}$ α-olefin, and especially an ethylene/$C_4$–$C_8$ α-olefin copolymer such as an ethylene/1-octene copolymer, ethylene/1-butene copolymer, ethylene/1-pentene copolymer or ethylene/1-hexene copolymer.

Suitable homogeneously branched linear ethylene polymers for use in the invention are sold under the designation of TAFMER by Mitsui Chemical Corporation and under the designations of EXACT and EXCEED resins by Exxon Chemical Company.

The term "substantially linear ethylene polymer" as used herein means that the bulk ethylene polymer is substituted, on average, with about 0.01 long chain branches/1000 total carbons to about 3 long chain branches/1000 total carbons (wherein "total carbons" includes both backbone and branch carbons). Preferred polymers are substituted with about 0.01 long chain branches/1000 total carbons to about 1 long chain branches/1000 total carbons, more preferably from about 0.05 long chain branches/1000 total carbons to about 1 long chain branched/1000 total carbons, and especially from about 0.3 long chain branches/1000 total carbons to about 1 long chain branches/1000 total carbons.

As used herein, the term "backbone" refers to a discrete molecule, and the term "polymer" or "bulk polymer" refers, in the conventional sense, to the polymer as formed in a reactor. For the polymer to be a "substantially linear ethylene polymer", the polymer must have at least enough molecules with long chain branching such that the average long chain branching in the bulk polymer is at least an average of from about 0.01/1000 total carbons to about 3 long chain branches/1000 total carbons.

The term "bulk polymer" as used herein means the polymer which results from the polymerization process as a mixture of polymer molecules and, for substantially linear ethylene polymers, includes molecules having an absence of long chain branching as well as molecules having long chain branching. Thus a "bulk polymer" includes all molecules formed during polymerization. It is understood that, for the substantially linear polymers, not all molecules have long chain branching, but a sufficient amount do such that the average long chain branching content of the bulk polymer positively affects the melt rheology (i.e., the shear viscosity and melt fracture properties) as described herein below and elsewhere in the literature.

Long chain branching (LCB) is defined herein as a chain length of at least one (1) carbon less than the number of carbons in the comonomer, whereas short chain branching (SCB) is defined herein as a chain length of the same number of carbons in the residue of the comonomer after it is incorporated into the polymer molecule backbone. For example, a substantially linear ethylene/1-octene polymer has backbones with long chain branches of at least seven (7) carbons in length, but it also has short chain branches of only six (6) carbons in length.

Long chain branching can be distinguished from short chain branching by using $^{13}C$ nuclear magnetic resonance (NMR) spectroscopy and to a limited extent, e.g. for ethylene homopolymers, it can be quantified using the method of Randall, (Rev. Macromol. Chem. Phys., C29 (2&3), p. 285–297 (1989)), the disclosure of which is incorporated herein by reference. However as a practical matter, current $^{13}C$ nuclear magnetic resonance spectroscopy cannot determine the length of a long chain branch in excess of about six (6) carbon atoms and as such, this analytical technique cannot distinguish between a seven (7) carbon branch and a seventy (70) carbon branch. The long chain branch can be as long as about the same length as the length of the polymer backbone.

Although conventional 13C nuclear magnetic resonance spectroscopy cannot determine the length of a long chain branch in excess of six carbon atoms, there are other known techniques useful for quantifying or determining the presence of long chain branches in ethylene polymers, including ethylene/1-octene interpolymers. For example, U.S. Pat. No. 4,500,648, incorporated herein by reference, teaches that long chain branching frequency (LCB) can be represented by the equation $LCE=b/M_w$ wherein b is the weight average number of long chain branches per molecule and $M_w$ is the weight average molecular weight. The molecular weight averages and the long chain branching characteristics are determined by gel permeation chromatography and intrinsic viscosity methods, respectively.

Two other useful methods for quantifying or determining the presence of long chain branches in ethylene polymers, including ethylene/1-octene interpolymers are gel permeation chromatography coupled with a low angle laser light scattering detector (GPC-LALLS) and gel permeation chromatography coupled with a differential viscometer detector (GPC-DV). The use of these techniques for long chain branch detection and the underlying theories have been well documented in the literature. See, e.g., Zimm, G. H. and Stockmayer, W. H., *J. Chem. Phys.* 17, 1301 (1949) and Rudin, A., *Modern Methods of Polymer Characterization*, John Wiley & Sons, New York (1991) pp. 103–112, the disclosures of both of which are incorporated by reference.

A. Willem degroot and P. Steve Chum, both of The Dow Chemical Company, at the Oct. 4, 1994 conference of the Federation of Analytical Chemistry and Spectroscopy Society (FACSS) in St. Louis, Mo., presented data demonstrating that GPC-DV is indeed a useful technique for quantifying the presence of long chain branches in substantially linear ethylene polymers. In particular, deGroot and Chum found that the level of long chain branches in substantially linear ethylene homopolymer samples measured using the Zimm-Stockmayer equation correlated well with the level of long chain branches measured using $^{13}C$ NMR.

Further, deGroot and Chum found that the presence of octene does not change the hydrodynamic volume of the polyethylene samples in solution and, as such, one can account for the molecular weight increase attributable to octene short chain branches by knowing the mole percent octene in the sample. By deconvoluting the contribution to molecular weight increase attributable to 1-octene short chain branches, deGroot and Chum showed that GPC-DV may be used to quantify the level of long chain branches in substantially linear ethylene/octene copolymers.

DeGroot and Chum also showed that a plot of Log ($I_2$, melt index) as a function of Log (GPC Weight Average Molecular Weight) as determined by GPC-DV illustrates that the long chain branching aspects (but not the extent of long branching) of substantially linear ethylene polymers are comparable to that of high pressure, highly branched low density polyethylene (LDPE) and are clearly distinct from ethylene polymers produced using Ziegler-type catalysts such as titanium complexes and ordinary homogeneous catalysts such as hafnium and vanadium complexes.

For substantially linear ethylene polymers, the empirical effect of the presence of long chain branching is manifested as enhanced rheological properties which are quantified and expressed in terms of gas extrusion rheometry (GER) results and/or melt flow, $I_{10}/I_2$, increases.

The substantially linear ethylene polymers used in the present invention are a unique class of compounds that are further defined in U.S. Pat. No. 5,272,236, application Ser. No. 07/776,130, filed Oct. 15, 1991; U.S. Pat. No. 5,278,272, application Ser. No. 07/939,281, filed Sep. 2, 1992; and U.S. Pat. No. 5,665,800, application Ser. No. 08/730,766, filed Oct. 16, 1996, each of which is incorporated herein by reference.

Substantially linear ethylene polymers differ significantly from the class of polymers conventionally known as homogeneously branched linear ethylene polymers described above and, for example, by Elston in U.S. Pat. No. 3,645,992. As an important distinction, substantially linear ethylene polymers do not have a linear polymer backbone in the conventional sense of the term "linear" as is the case for homogeneously branched linear ethylene polymers.

Substantially linear ethylene polymers also differ significantly from the class of polymers known conventionally as heterogeneously branched traditional Ziegler polymerized linear ethylene interpolymers (for example, ultra low density polyethylene, linear low density polyethylene or high density polyethylene made, for example, using the technique disclosed by Anderson et al. in U.S. Pat. No. 4,076,698, in that substantially linear ethylene interpolymers are homogeneously branched polymers. Further, substantially linear ethylene polymers also differ from the class of heterogeneously branched ethylene polymers in that substantially linear ethylene polymers are characterized as essentially lacking a measurable high density or crystalline polymer fraction as determined using a temperature rising elution fractionation technique.

The homogeneously branched substantially linear ethylene polymers for use in the present invention is characterized as having (a) melt flow ratio, $I_{10}/I_2 \geq 5.63$, (b) a molecular weight distribution, $M_w/M_n$, as determined by gel permeation chromatography and defined by the equation:

$$(M_w/M_n) \leq (I_{10}/I_2) - 4.63,$$

(c) a gas extrusion rheology such that the critical shear rate at onset of surface melt fracture for the substantially linear ethylene polymer is at least 50 percent greater than the critical shear rate at the onset of surface melt fracture for a linear ethylene polymer, wherein the substantially linear ethylene polymer and the linear ethylene polymer comprise the same comonomer or comonomers, the linear ethylene polymer has an $I_2$ and $M_w/M_n$ within ten percent of the substantially linear ethylene polymer and wherein the respective critical shear rates of the substantially linear ethylene polymer and the linear ethylene polymer are measured at the same melt temperature using a gas extrusion rheometer, (d) a single differential scanning calorimetry, DSC, melting peak between $-30°$ and $150°$ C., and (e) a density less than or equal to $0.865$ g/cm$^3$.

Determination of the critical shear rate and critical shear stress in regards to melt fracture as well as other rheology properties such as "rheological processing index" (PI), is performed using a gas extrusion rheometer (GER). The gas extrusion rheometer is described by M. Shida, R. N. Shroff and L. V. Cancio in *Polymer Engineering Science*, Vol. 17, No. 11, p. 770 (1977) and in *Rheometers for Molten Plastics* by John Dealy, published by Van Nostrand Reinhold Co. (1982) on pp. 97–99, the disclosures of both of which are incorporated herein by reference.

The processing index (PI) is measured at a temperature of 190° C., at nitrogen pressure of 2500 psig using a 0.0296 inch (752 micrometers) diameter (preferably a 0.0143 inch diameter die for high flow polymers, e.g. 50–100 $I_2$ melt index or greater), 20:1 L/D die having an entrance angle of 180°. The GER processing index is calculated in millipoise units from the following equation:

$$PI = 2.15 \times 10^6 \ dyne/cm^2/(1000 \times shear \ rate),$$

where: $2.15 \times 10^6$ dyne/cm$^2$ is the shear stress at 2500 psi, and the shear rate is the shear rate at the wall as represented by the following equation:

$$32 \ Q'/(60 \ sec/min)(0.745)(Diameter \times 2.54 \ cm/in)^3, \ where:$$

Q' is the extrusion rate (gms/min),
0.745 is the melt density of polyethylene (gm/cm$^3$), and Diameter is the orifice diameter of the capillary (inches).

The PI is the apparent viscosity of a material measured at apparent shear stress of $2.15 \times 10^6$ dyne/cm$^2$.

For substantially linear ethylene polymers, the PI is less than or equal to 70 percent of that of a conventional linear ethylene polymer having an $I_2$, $M_w/M_n$ and density each within ten percent of the substantially linear ethylene polymer.

An apparent shear stress vs. apparent shear rate plot is used to identify the melt fracture phenomena over a range of nitrogen pressures from 5250 to 500 psig using the die or GER test apparatus previously described. According to Ramamurthy in *Journal of Rheology*, 30(2), 337–357, 1986, above a certain critical flow rate, the observed extrudate irregularities may be broadly classified into two main types: surface melt fracture and gross melt fracture.

Surface melt fracture occurs under apparently steady flow conditions and ranges in detail from loss of specular gloss to the more severe form of "sharkskin". In this disclosure, the onset of surface melt fracture is characterized at the beginning of losing extrudate gloss at which the surface roughness of extrudate can only be detected by 40× magnification. The critical shear rate at onset of surface melt fracture for the substantially linear ethylene polymers is at least 50 percent greater than the critical shear rate at the onset of surface melt fracture of a linear ethylene polymer having about the same $I_2$ and $M_w/M_n$. Preferably, the critical shear stress at onset of surface melt fracture for the substantially linear ethylene polymers of the invention is greater than about $2.8 \times 10^6$ dyne/cm$^2$.

Gross melt fracture occurs at unsteady flow conditions and ranges in detail from regular (alternating rough and smooth, helical, etc.) to random distortions. For commercial acceptability, (e.g., in blown film products), surface defects should be minimal, if not absent. The critical shear rate at onset of surface melt fracture (OSMF) and critical shear stress at onset of gross melt fracture (OGMF) will be used herein based on the changes of surface roughness and configurations of the extrudates extruded by a GER. For the substantially linear ethylene polymers used in the invention, the critical shear stress at onset of gross melt fracture is preferably greater than about $4 \times 10^6$ dyne/cm$^2$.

For the processing index determination and for the GER melt fracture determination, substantially linear ethylene polymers are tested without inorganic fillers and do not have more than 20 ppm aluminum catalyst residue. Preferably, however, for the processing index and melt fracture tests, substantially linear ethylene polymers do contain antioxidants such as phenols, hindered phenols, phosphites or phosphonites, preferably a combination of a phenol or hindered phenol and a phosphite or a phosphonite.

The molecular weight distributions of ethylene polymers are determined by gel permeation chromatography (GPC) on a Waters 150 C. high temperature chromatographic unit equipped with a differential refractometer and three columns of mixed porosity. The columns are supplied by Polymer Laboratories and are commonly packed with pore sizes of $10^3$, $10^4$, $10^5$ and $10^6$ Å. The solvent is 1,2,4-trichlorobenzene, from which about 0.3 percent by weight solutions of the samples are prepared for injection. The flow rate is about 1.0 milliliters/minute, unit operating temperature is about 140° C. and the injection size is about 100 microliters.

The molecular weight determination with respect to the polymer backbone is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Ward in *Journal of Polymer Science*, Polymer Letters, Vol. 6, p. 621, 1968, the disclosure of which is incorporated herein by reference) to derive the following equation:

$$M_{polyethylene} = a * (M_{polystyrene})^b.$$

In this equation, a=0.4316 and b=1.0. Weight average molecular weight, $M_w$, is calculated in the usual manner according to the following formula: $M_j = (\Sigma w_i(M_i^j))^j$. Where $w_i$ is the weight fraction of the molecules with molecular weight $M_i$ eluting from the GPC column in fraction i and j=1 when calculating $M_w$ and j=−1 when calculating $M_n$.

For the at least one homogeneously branched ethylene polymer used in the present invention, the $M_w/M_n$ is preferably less than 3.5, more preferably less than 3.0, most preferably less than 2.5, and especially in the range of from about 1.5 to about 2.5 and most especially in the range from about 1.8 to about 2.3.

Substantially linear ethylene polymers are known to have excellent processability, despite having a relatively narrow molecular weight distribution (that is, the $M_w/M_n$ ratio is typically less than about 3.5). Surprisingly, unlike homogeneously and heterogeneously branched linear ethylene polymers, the melt flow ratio ($I_{10}/I_2$) of substantially linear ethylene polymers can be varied essentially independently of the molecular weight distribution, $M_w/M_n$. Accordingly, especially when good extrusion processability is desired, the preferred ethylene polymer for use in the present invention is a homogeneously branched substantially linear ethylene interpolymer.

Suitable constrained geometry catalysts for use manufacturing substantially linear ethylene polymers include constrained geometry catalysts as disclosed in U.S. application Ser. No. 07/545,403, filed Jul. 3, 1990pending; U.S. application Ser. No. 07/758,654, filed Sep. 12, 1991 now U.S. Pat. No. 5,132,380 U.S. Pat. No. 5,064,802 (application Ser. No. 07/547,728); U.S. Pat. No. 5,470,993 (application Ser. No. 08/241,523); U.S. Pat. No. 5,453,410 (application Ser. No. 08/108,693); U.S. Pat. No. 5,374,696 (application Ser. No. 08/08,003); U.S. Pat. No. 5,532,394 (application Ser. No. 08/295,768); U.S. Pat. No. 5,494,874 (application Ser. No. 08/294,469); and U.S. Pat. No. 5,189,192 (application Ser. No. 07/647,111), the teachings of all of which are incorporated herein by reference.

Suitable catalyst complexes may also be prepared according to the teachings of WO 93/08199, and the patents issuing therefrom, all of which are incorporated herein by reference. Further, the monocyclopentadienyl transition metal olefin polymerization catalysts taught in U.S. Pat. No. 5,026,798, which is incorporated herein by reference, are also believed to be suitable for use in preparing the polymers of the present invention, so long as the polymerization conditions substantially conform to those described in U.S. Pat. Nos. 5,272,236; 5,278,272 and 5,665,800, especially with strict attention to the requirement of continuous polymerization. Such polymerization methods are also described in PCT/US 92/08812 (filed Oct. 15, 1992).

The foregoing catalysts may be further described as comprising a metal coordination complex comprising a metal of groups 3–10 or the Lanthanide series of the Periodic Table of the Elements and a delocalize β-bonded moiety substituted with a constrain-inducing moiety, said complex having a constrained geometry about the metal atom such that the angle at the metal between the centroid of the delocalized, substituted pi-bonded moiety and the center of at least one remaining substituent is less than such angle in a similar complex containing a similar pi-bonded moiety lacking in such constrain-inducing substituent, and provided further that for such complexes comprising more than one delocalized, substituted pi-bonded moiety, only one thereof for each metal atom of the complex is a cyclic, delocalized, substituted pi-bonded moiety. The catalyst further comprises an activating cocatalyst.

Suitable cocatalysts for use herein include polymeric or oligomeric aluminoxanes, especially methyl aluminoxane, as well as inert, compatible, noncoordinating, ion forming compounds. So-called modified methyl aluminoxane (MMAO) is also suitable for use as a cocatalyst. One technique for preparing such modified aluminoxane is disclosed in U.S. Pat. No. 5,041,584, the disclosure of which is incorporated herein by reference. Aluminoxanes can also be made as disclosed in U.S. Pat. Nos. 5,218,071; 5,086,024; 5,041,585; 5,041,583; 5,015,749; 4,960,878; and 4,544,762, the disclosures of all of which are incorporated herein by reference.

Aluminoxanes, including modified methyl aluminoxanes, when used in the polymerization, are preferably used such that the catalyst residue remaining in the (finished) polymer is preferably in the range of from about 0 to about 20 ppm aluminum, especially from about 0 to about 10 ppm aluminum, and more preferably from about 0 to about 5 ppm aluminum. In order to measure the bulk polymer properties (e.g. PI or melt fracture), aqueous HCL is used to extract the aluminoxane from the polymer. Preferred cocatalysts, however, are inert, noncoordinating, boron compounds such as those described in EP 520732, the disclosure of which is incorporated herein by reference.

Substantially linear ethylene are produced via a continuous (as opposed to a batch) controlled polymerization process using at least one reactor (e.g., as disclosed in WO 93/07187, WO 93/07188, and WO 93/07189, the disclosure of each of which is incorporated herein by reference), but can also be produced using multiple reactors (e.g., using a multiple reactor configuration as described in U.S. Pat. No. 3,914,342, the disclosure of which is incorporated herein by reference) at a polymerization temperature and pressure sufficient to produce the interpolymers having the desired properties. The multiple reactors can be operated in series or in parallel, with at least one constrained geometry catalyst employed in at least one of the reactors.

Substantially linear ethylene polymers can be prepared via the continuous solution, slurry, or gas phase polymerization in the presence of a constrained geometry catalyst, such as the method disclosed in EP 416,815-A, the disclosure of which is incorporated herein by reference. The polymerization can generally be performed in any reactor system known in the art including, but not limited to, a tank reactor(s), a sphere reactor(s), a recycling loop reactor(s) or combinations thereof and the like, any reactor or all reactors operated partially or completely adiabatically, nonadiabatically or a combination of both and the like. Preferably, a continuous loop-reactor solution polymerization process is used to manufacture the substantially linear ethylene polymer used in the present invention.

In general, the continuous polymerization required to manufacture substantially linear ethylene polymers may be accomplished at conditions well known in the prior art for Ziegler-Natta or Kaminsky-Sinn type polymerization reactions, that is, temperatures from 0 to 250° C. and pressures from atmospheric to 1000 atmospheres (100 MPa). Suspension, solution, slurry, gas phase or other process conditions may be employed if desired.

A support may be employed in the polymerization, but preferably the catalysts are used in a homogeneous (i.e., soluble) manner. It will, of course, be appreciated that the active catalyst system forms in situ if the catalyst and the cocatalyst components thereof are added directly to the polymerization process and a suitable solvent or diluent, including condensed monomer, is used in said polymerization process. It is, however, preferred to form the active catalyst in a separate step in a suitable solvent prior to adding the same to the polymerization mixture.

The substantially linear ethylene polymers used in the present invention are interpolymers of ethylene with at least one $C_3$–$C_{20}$ α-olefin and/or $C_4$–$C_{18}$ diolefin. Copolymers of ethylene and an α-olefin of $C_3$–$C_{20}$ carbon atoms are especially preferred. The term "interpolymer" as discussed above is used herein to indicate a copolymer, or a terpolymer, or the like, where, at least one other comonomer is polymerized with ethylene or propylene to make the interpolymer.

Suitable unsaturated comonomers useful for polymerizing with ethylene include, for example, ethylenically unsaturated monomers, conjugated or non-conjugated dienes, polyenes, etc. Examples of such comonomers include $C_3$–$C_{20}$ α-olefins such as propylene, isobutylene, 1-butene, 1-hexene, 1-pentene, 4-methyl-1-pentene, 1-heptene, 1-octene, 1-nonene, 1-decene, and the like. Preferred comonomers include propylene, 1-butene, 1-pentene, 1-hexene, 4-methyl-1-pentene, 1-heptene, and 1-octene, and 1-octene is especially preferred. Other suitable monomers include styrene, halo- or alkyl-substituted styrenes, vinylbenzocyclobutane, 1,4-hexadiene, 1,7-octadiene, and naphthenics (e.g., cyclopentene, cyclohexene and cyclooctene).

The ethylene interpolymer can be blended with other polymers. Suitable polymers for blending with the ethylene interpolymer are commercially available from a variety of suppliers and include, but are not limited, an ethylene polymer (e.g., low density polyethylene, ultra or very low density polyethylene, medium density polyethylene, linear low density polyethylene, high density polyethylene, homogeneously branched linear ethylene polymer, substantially linear ethylene polymer, polystyrene, ethylene styrene interpolymer, ethylene vinyl acetate interpolymer, ethylene acrylic acid interpolymer, ethylene ethyl acetate interpolymer, ethylene methacrylic acid interpolymer, ethylene methacrylic acid ionomer, and the like), polycarbonate, polystyrene, polypropylene (e.g., homopolymer polypropylene, polypropylene copolymer, random block polypropylene interpolymer and the like), thermoplastic polyurethane, polyamide, polylactic acid interpolymer, thermoplastic block polymer (e.g. styrene butadiene copolymer, styrene butadiene styrene triblock copolymer, styrene ethylene-butylene styrene triblock copolymer and the like), polyether block copolymer (e.g., PEBAX), copolyester polymer, polyester/polyether block polymers (e.g., HYTREL), ethylene carbon monoxide interpolymer (e.g., ethylene/carbon monoxide (ECO), copolymer, ethylene/acrylic acid/carbon monoxide (EAACO) terpolymer, ethylene/methacrylic acid/carbon monoxide (EMAACO) terpolymer, ethylene/vinyl acetate/carbon monoxide (EVACO) terpolymer and styrene/carbon monoxide (SCO)), polyethylene terephthalate (PET), chlorinated polyethylene, and the like and mixtures thereof.

In one preferred embodiment, the ethylene interpolymer is blended with a polypropylene resins. Suitable polypropylene polymers for use in the invention, including random block propylene ethylene polymers, are available from a number of manufacturers, such as, for example, Montell Polyolefins and Exxon Chemical Company. At Exxon, suitable polypropylene polymers are supplied under the designations ESCORENE and ACHIEVE.

Suitable poly lactic acid (PLA) polymers for use in the invention are well known in the literature (e.g., see D. M. Bigg et al., "Effect of Copolymer Ratio on the Crystallinity and Properties of Polylactic Acid Copolymers", ANTEC '96, pp. 2028–2039; WO 90/01521; EP 0 515203A; and EP 0 748846A2, the disclosures of each of which are incorporated herein by reference). Suitable poly lactic acid polymers are supplied commercially by Cargill Dow under the designation EcoPLA.

Suitable thermoplastic polyurethane for use in the invention are commercially available from The Dow Chemical Company under the designation PELLATHANE.

Suitable polyolefin carbon monoxide interpolymers can be manufactured using well known high pressure free-radical polymerization methods. However, they may also be manufactured using traditional Ziegler-Natta catalysis and even with the use of so-called homogeneous catalyst systems such as those described and referenced herein above.

Suitable free-radical initiated high pressure carbonyl-containing ethylene polymers such as ethylene acrylic acid interpolymers can be manufactured by any technique known in the art including the methods taught by Thomson and Waples in U.S. Pat. No. 3,520,861 and by McKinney et al. in U.S. Pat. Nos. 4,988,781; 4,599,392; and 5,384,373, the disclosures of which are incorporated herein by reference.

Suitable ethylene vinyl acetate interpolymers for use in the invention are commercially available from various suppliers, including Exxon Chemical Company and Du Pont Chemical Company.

Suitable ethylene/alkyl acrylate interpolymers are commercially available from various suppliers. Suitable ethylene/acrylic acid interpolymers are commercially available from The Dow Chemical Company under the designation PRIMACOR. Suitable ethylene/methacrylic acid interpolymers are commercially available from Du Pont Chemical Company under the designation NUCREL.

Chlorinated polyethylene (CPE), especially chlorinated substantially linear ethylene polymers, can be prepared by chlorinating polyethylene in accordance with well known techniques. Preferably, chlorinated polyethylene comprises equal to or greater than 30 weight percent chlorine. Suitable chlorinated polyethylenes for use in the invention are commercially supplied by The Dow Chemical Company under the designation TYRIN.

Additives e.g., Irgafos® 168 or Irganox® 1010 supplied by Ciba Geigy Corp., may be added to the ethylene polymer protect against undo degradation during shaping or fabrication operation and/or to better control the extent of grafting or crosslinking (i.e., inhibit excessive gelation). In-process additives, e.g. calcium stearate, water, fluoropolymers, etc., may also be used for purposes such as for the deactivation of residual catalyst and/or improved processability.

The ethylene interpolymer can be filled or unfilled. If filled, then the amount of filler present should not exceed an amount that would adversely affect elevated temperature elasticity. Typically, the amount of filler present is between 20 and 80, preferably between 50 and 70, weight percent (wt percent) based on the total weight of the interpolymer. Representative fillers include kaolin clay, magnesium hydroxide, silica, calcium carbonate. In a preferred embodiment, in which a filler is present, the filler is coated with a material that will prevent or retard any tendency that the filler might otherwise have to interfere with the crosslinking reactions. Stearic acid is illustrative of such a filler coating.

The elastic ethylene interpolymer and elastic article of the invention have utility in a variety of applications. Suitable applications include, for example, but are not limited to, disposable personal hygiene products (e.g. training pants, diapers, absorbent underpants, incontinence products, feminine hygiene items and the like); disposable garments (e.g. industrial apparel, coveralls, head coverings, underpants, pants, shirts, gloves, socks and the like); infection control/clean room products (e.g. surgical gowns and drapes, face masks, head coverings, surgical caps and hood, shoe coverings, boot slippers, wound dressings, bandages, sterilization wraps, wipers, lab coats, coverall, pants, aprons, jackets, bedding items and sheets and the like) and sports apparel.

Various homofil fibers can be made from the elastic ethylene interpolymer of the present invention, including staple fibers, spunbond fibers or melt blown fibers (using, e.g., systems as disclosed in U.S. Pat. No. 4,340,563 (Appel et al.), U.S. Pat. No. 4,663,220 (Wisneski et al.), U.S. Pat. No. 4,668,566 (Braun), or U.S. Pat. No. 4,322,027 (Reba), all of which are incorporated herein by reference), and gel spun fibers (e.g., the system disclosed in U.S. Pat. No. 4,413,110 (Kavesh et al.), incorporated herein by reference)). Staple fibers can be melt spun (i.e., they can be extruded into the final fiber diameter directly without additional drawing), or they can be melt spun into a higher diameter and subsequently hot or cold drawn to the desired diameter using conventional fiber drawing techniques.

Elastic staple fibers of the present invention herein can also be used as bonding fibers, especially where the inventive elastic fibers have a lower melting point than the surrounding matrix fibers. In a bonding fiber application, the bonding fiber is typically blended with other matrix fibers and the entire structure is subjected to heat, where the bonding fiber melts and bonds the surrounding matrix fiber. Typical matrix fibers which benefit from use of the inventive elastic fibers disclosed herein include, but are not limited to, poly(ethylene terephthalate) fibers, cotton fibers, nylon fibers, polypropylene fibers, heterogeneously branched polyethylene fibers, homogeneously branched ethylene polymer fibers, linear polyethylene homopolymer fibers and the like and combinations thereof. The diameter of the matrix fiber can vary depending upon the end use application.

Bicomponent fibers can also be made from the novel homogeneously branched substantially linear ethylene polymers. Such bicomponent fibers have the elastic ethylene interpolymer of the present invention in at least one portion of the fiber. For example, in a sheath/core bicomponent fiber (i.e., one in which the sheath concentrically surrounds the core), the elastic ethylene interpolymer can be in either the sheath or the core. Different elastic ethylene interpolymers of the present invention can also be used independently as the sheath and the core in the same fiber, preferably where both components are elastic and especially where the sheath component has a lower melting point than the core component. Other types of bicomponent fibers are within the scope of the invention as well, and include such structures as side-by-side conjugated fibers (e.g., fibers having separate regions of polymers, wherein the elastic ethylene interpolymer of the present invention comprises at least a portion of the fiber's surface).

The shape of the fiber is not limited. For example, typical fiber has a circular cross-sectional shape, but sometimes fibers have different shapes, such as a trilobal shape, or a flat (i.e., "ribbon" like) shape. The elastic fiber disclosed herein is not limited by the shape of the fiber.

The heat resistant elastic fiber of the present invention can be used with other fibers such as PET, Nylon, cotton, etc. to make elastic fabrics. As an added advantage, the heat (and moisture) resistance of the elastic fiber of present invention can enable polyester PET fibers to be dyed at ordinary PET dyeing conditions. The other commonly used elastic fibers, especially spandex, can only be used at less severe PET dyeing conditions to prevent degradation of properties.

Fiber diameter can be measured and reported in a variety of fashions. Generally, fiber diameter is measured in denier per filament. Denier is a textile term which is defined as the grams of the fiber per 9000 meters of that fiber's length. Monofilament generally refers to an extruded strand having a denier per filament greater than 15, usually greater than 30. Fine denier fiber generally refers to fiber having a denier of about 15 or less. Microdenier (aka microfiber) generally refers to fiber having a diameter not greater than about 100 micrometers. For the inventive elastic fibers disclosed herein, the diameter can be widely varied, with little impact upon the fiber's elasticity. But the fiber denier can be adjusted to suit the capabilities of the finished article and as such, would preferably be: from about 0.5 to about 30 denier/filament for melt blown; from about 1 to about 30 denier/filament for spunbond; and from about 1 to about 20,000 denier/filament for continuous wound filament. Nonetheless, preferably, the nominal denier is greater than 37, more preferably greater than or equal to 55 and most preferably greater than or equal to 65. These preference are due to the fact that typically durable apparel employ fibers with deniers greater than or equal to about 40.

Fabrics made from the inventive elastic fibers disclosed herein include both woven and nonwoven fabrics. Nonwoven fabrics can be made variously, including spunlaced (or hydrodynamically entangled) fabrics as disclosed in U.S. Pat. No. 3,485,706 (Evans) and U.S. Pat. No. 4,939,016 (Radwanski et al.), the disclosures of which are incorporated herein by reference; by carding and thermally bonding staple fibers; by spunbonding continuous fibers in one continuous operation; or by melt blowing fibers into fabric and subsequently calandering or thermally bonding the resultant web. These various nonwoven fabric manufacturing techniques are well known to those skilled in the art and the disclosure is not limited to any particular method. Other structures made from such fibers are also included within the scope of the invention, including e.g., blends of these novel fibers with other fibers (e.g., poly(ethylene terephthalate) (PET) or cotton).

Fabricated articles which can be made using the inventive elastic fibers and fabrics disclosed herein include elastic composite articles (e.g., diapers) that have elastic portions. For example, elastic portions are typically constructed into diaper waist band portions to prevent the diaper from falling and leg band portions to prevent leakage (as shown in U.S. Pat. No. 4,381,781 (Sciaraffa), the disclosure of which is incorporated herein by reference). Often, the elastic portions promote better form fitting and/or fastening systems for a good combination of comfort and reliability. The inventive elastic fibers and fabrics disclosed herein can also produce structures which combine elasticity with breathability. For example, the inventive elastic fibers, fabrics and/or films of the present invention many be incorporated into the structures disclosed in U.S. Pat. No. 6,176,952, the disclosure of which is incorporated herein by reference.

The inventive elastic fibers and fabrics disclosed herein can also be used in various structures as described in U.S. Pat. No. 2,957,512 (Wade), the disclosure of which is incorporated herein by reference. For example, layer 50 of the structure described in U.S. Pat. No. '512 (i.e., the elastic component) can be replaced with the inventive elastic fibers and fabrics, especially where flat, pleated, creped, crimped, etc., nonelastic materials are made into elastic structures. Attachment of the inventive elastic fibers and/or fabric disclosed herein to nonelastic fibers, fabrics or other structures can be done by melt bonding or with adhesives. Gathered or shirred elastic structures can be produced from the inventive elastic fibers and/or fabrics disclosed herein and nonelastic components by pleating the non-elastic component (as described in U.S. Pat. No. '512) prior to attachment, pre-stretching the elastic component prior to attachment, or heat shrinking the elastic component after attachment.

The inventive elastic fibers described herein also can be used in a spunlaced (or hydrodynamically entangled) process to make novel structures. For example, U.S. Pat. No. 4,801,482 (Goggans), the disclosure of which is incorporated herein by reference, discloses an elastic sheet (12) which can now be made with the novel elastic fibers/fabric described herein.

Continuous elastic filaments as described herein could also be used in woven applications where high resilience is desired.

The inventive elastic fibers and fabrics disclosed herein with adjust in the interpolymer melt index and/or degree of crosslinking or extent or radiation also have adjustable tenacity and retractive force. Such capabilities and characteristics enable extensive design flexibility, for example, to provide for variable retractive force in the same garment, if needed, as described for example in U.S. Pat. No. 5,196,000 (Clear et al.), the disclosure of which is incorporated herein by reference.

U.S. Pat. No. 5,037,416 (Allen et al.), the disclosure of which is incorporated herein by reference, describes the advantages of a form fitting top sheet by using elastic ribbons (see member 19 of U.S. Pat. No. '416). The inventive elastic fibers could serve the function of member 19 of U.S. Pat. No. '416, or could be used in fabric form to provide the desired elasticity.

Composites that utilize very high molecular weight linear polyethylene or copolymer polyethylene also benefit from the inventive elastic fibers disclosed herein. For example, the inventive elastic fibers have a low melting point (with the melting point of the polymer essentially linearly related to the polymer density), such that in a blend of inventive elastic fibers disclosed herein and very high molecular weight polyethylene fibers (e.g., Spectra™ fibers made by Allied Chemical) as described in U.S. Pat. No. 4,584,347 (Harpell et al.), the disclosure of which is incorporated herein by reference, the lower melting elastic fibers bond the high molecular weight polyethylene fibers without melting the high molecular weight fibers, thus preserving the high strength and integrity of the high molecular weight fiber.

In U.S. Pat. No. 4,981,747 (Morman), the inventive elastic fibers and/or fabrics disclosed herein can be substituted for elastic sheet 122, which forms a composite elastic material including a reversibly necked material.

The inventive elastic fibers disclosed herein can also be a melt blown elastic component, as described in reference 6 of the drawings of U.S. Pat. No. 4,879,170 (Radwanski), the disclosure of which is incorporated herein by reference. U.S. Pat. No. '170 generally describes elastic co-form material and manufacturing processes.

Elastic panels can also be made from the inventive elastic fibers and fabrics disclosed herein, and can be used, for example, as members 18, 20, 14, and/or 26 of U.S. Pat. No.

4,940,464 (Van Gompel), the disclosure of which is incorporated herein by reference. The inventive elastic fibers and fabrics described herein can also be used as elastic components of composite side panels (e.g., layer 86 of U.S. Pat. No. '464).

The elastic ethylene polymer can also be shaped or fabricated into elastic films, coatings, sheets, strips, tapes, ribbons and the like. The elastic film, coating and sheet of the present invention may be fabricated by any method known in the art, including blown bubble processes (e.g., simple bubble as well as biaxial orientation techniques such trapped bubble, double bubble and tenter framing), cast extrusion, injection molding processes, thermoforming processes, extrusion coating processes, profile extrusion, and sheet extrusion processes. Simple blown bubble film processes are described, for example, in *The Encyclopedia of Chemical Technology*, Kirk-Othmer, Third Edition, John Wiley & Sons, New York, 1981, Vol. 16, pp. 416417 and Vol. 18, pp. 191–192. The cast extrusion method is described, for example, in Modern Plastics Mid-October 1989 Encyclopedia Issue, Volume 66, Number 11, pages 256 to 257. Injection molding, thermoforming, extrusion coating, profile extrusion, and sheet extrusion processes are described, for example, in Plastics Materials and Processes, Seymour S. Schwartz and Sidney H. Goodman, Van Nostrand Reinhold Company, New York, 1982, pp. 527–563, pp. 632–647, and pp. 596–602.

The elastic strips, tapes and ribbons of the present invention can be prepared by any known method, including the direct extrusion processing or by post-extrusion slitting, cutting or stamping techniques. Profile extrusion is an example of a primary extrusion process that is particularly suited to the preparation of tapes, bands, ribbons and the like.

The elastic materials of the present invention can also be rendered pervious or "breathable" by any method well known in the art including by apperturing, slitting, microperforating, mixing with fibers or foams, incorporating fillers and stretching or combinations thereof. Examples of such methods include, U.S. Pat. No. 3,156,242 by Crowe, Jr., U.S. Pat. No. 3,881,489 by Hartwell, U.S. Pat. No. 3,989,867 by Sisson and U.S. Pat. No. 5,085,654 by Buell, the disclosures of all of which are incorporate herein by reference.

Fabricated articles which can be made using the inventive elastic articles disclosed herein include composite fabric articles (e.g., disposable incontinence garments and diapers) that are comprised of one or more elastic component or portion. The inventive elastic articles disclosed herein can also produce fabric composite structures which combine elasticity with breathability by utilizing a technique that renders the elastic material pervious or "breathable" such as suggested by Lippert et al. in U.S. Pat. No. 4,861,652 and indicated above.

The inventive elastic articles disclosed herein can also be used in various structures as described in U.S. Pat. No. 2,957,512 (Wade), the disclosure of which is incorporated herein by reference. For example, layer 50 of the structure described in U.S. Pat. No. '512 (i.e., the elastic component) can be replaced with the novel elastic materials, especially where flat, pleated, creped, etc., nonelastic materials are made into elastic or semi-elastic structures. Attachment of the novel elastic materials to nonelastic or less-elastic materials can be done with heat bonding or with adhesives. Gathered or shirred elastic composite materials can be produced from the new elastic material described herein and nonelastic components by pleating the non-elastic component (as described in U.S. Pat. No. '512) prior to attachment, prestretching the elastic component prior to attachment, or heat shrinking the elastic component after attachment.

The recovery after heat shrinking can be further enhanced by effectuating a high degree of orientation into the inventive elastic articles during fabrication. Significant orientation can be accomplished by the utilization of various known techniques such as high blow-up blown film fabrication, tenter framing of cast films and "double bubble" or "trapped bubble" blown film fabrication.

The inventive elastic articles described herein can also be used make other novel structures. For example, U.S. Pat. No. 4,801,482 (Goggans), the disclosure of which is incorporated herein by reference, discloses an elastic sheet (12) which can now be made with the inventive elastic articles described herein.

The inventive elastic articles described herein can also be used to make breathable portion or breathable elastic composite materials. For example, U.S. Pat. No. 5,085,654 (Buell) discloses a leg band (15) with a breathable portion 45, a breathable topsheet (26), a breathable backsheet (25), elastic elements (31 and 64), a breathable element (54), and a breathable sub-element (96) all or any combination of which can now be made with the inventive elastic articles disclosed herein in either pervious or impervious forms.

U.S. Pat. No. 5,037,416 (Allen et al.), the disclosure of which is incorporated herein by reference, describes the advantages of a form fitting top sheet by using elastic ribbons (member 12) and an elastic backsheet (member 16). Pervious inventive elastic articles described herein could serve the function of member 12 and impervious elastics materials of this invention could function as member 16, or disclosed elastic materials could be used in an elastic composite fabric form.

In U.S. Pat. No. 4,981,747 (Morman), the inventive elastic articles disclosed herein can be substituted for elastic sheets 12, 122 and 232 to construct an elastic composite material which includes a reversibly necked material.

Elastic panels, elements, portions or the like can also be made from the inventive elastic articles disclosed herein, and can be used, for example, as members 18, 20, 24, and/or 26 of U.S. Pat. No. 4,940,464 (Van Gompel), the disclosure of which is incorporated herein by reference. The inventive elastic articles described herein can also be used, for example, as elastic composite side panels (e.g., layer) or as elastic ribbons 42 and/or 44.

The following examples are provided to further illustrate and illuminate the present invention but are not intended to limit the invention to the specific embodiments set forth.

EXAMPLES

In an evaluation to determine the elastic performance of various ethylene polymers in response to irradiation or crosslinking, five different ethylene interpolymers were subjected to varying degrees of electron beam radiation and their elastic properties as 2 mil cast films were measured at room temperature. The polymer densities and the melt indexes of the ethylene polymers are shown in Table 1. All of the polymers were homogeneously branched ethylene/1-octene interpolymers supplied commercially by Dupont Dow Elastomers, Ltd. and manufactured using a constrained geometry catalyst system. However, DDE 8190 also contained via blending 4–5 weight percent polypropylene. The densities for the various polymer were determined in accordance with ASTM D-792 and the melt indexes were determined in accordance with ASTM D-1238 Condition 190° C./2.16 kilograms.

TABLE 1

| Polymer | Density (g/cm$^3$) | Melt Index (g/10 minutes) | Designation |
|---|---|---|---|
| A | 0.863 | 0.5 | ENGAGE EG 8180 |
| B | 0.859 | 1.0 | DDE 8190 |
| C | 0.870 | 1.0 | ENGAGE EG 8100 |
| D | 0.870 | 5.0 | ENGAGE EG 8200 |
| E | 0.870 | 10 | XU-58380.00 |

2 mil cast films of each polymer listed in Table 1 were fabricated using conventional cast film extrusion equipment at melt temperatures of 430°–500° F. After film fabrication, the cast films were electron beam radiated at various dosage using equipment similar to that described in U.S. Pat. No. 5,324,576, the disclosure of which is incorporated herein by reference. The elastic properties (stress-strain dala) for the various films was determined using an Instron tensiometer set at 10 inch/minute, except as otherwise indicated.

For the permanent set determinations at 23° C., the gage length was 2 inches and the crosshead speed was 10 inches/minute. The test consisted of pulling the film sample to 200% strain (elongation) and holding it for 30 seconds, then returning the crosshead to the starting point and holding it for 60 seconds, and then pulling the sample to determine the point where the load initially rises above zero. The percent permanent set was taken as the percent strain at which the load rose above zero. The test was a one cycle test which was run in duplicate.

For percent stress or load relaxation determination at 23° C., the gage length was 2 inches and the crosshead speed was 10 inches/minute. This test consisted of pulling the film sample to 200% strain (elongation) and holding it for 30 seconds. The stress at initially at 200% strain was taken as the maximum stress and the stress after the 30 second holding period was taken as the minimum stress. The percent stress or load relaxation was run in duplicate and was calculated from the following equation:

$$\frac{\text{maximum stress} - \text{minimum stress}}{\text{maximum stress}} \times 100.$$

Table 2 reports the elastic property (stress-strain) data as as the permanent set and stress relaxation data for the various film samples.

Figure 2:
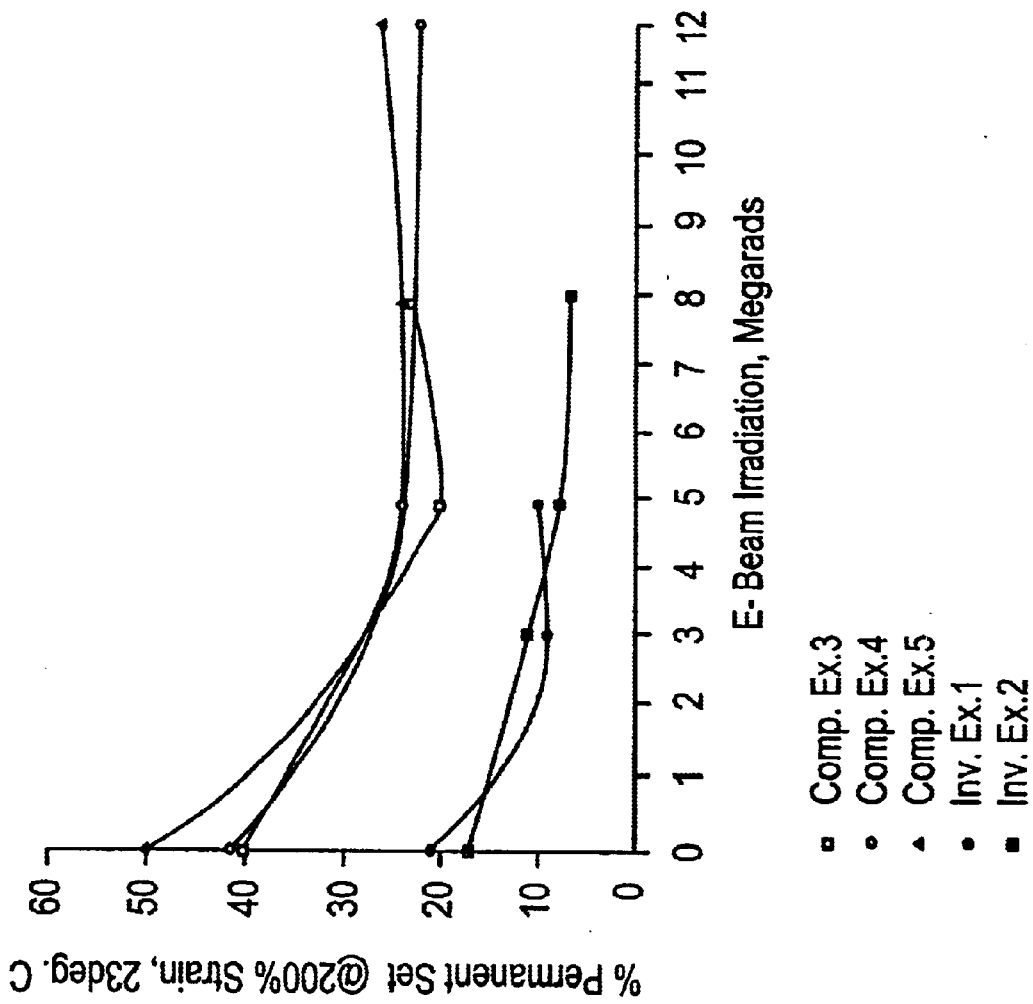
FIG. 2 is a plot of percent permanent set at 23° C. versus megarads of electron beam radiation for Inventive Examples 1 and 2 and comparative runs 3, 4 and 5.

Data in Table 2 was plotted and shown in FIGS. 1 and 2. FIG. 1 indicates that electron beam radiation up to 8–12 megarads has no substantial affect on the percent stress relaxation performance of the various polymers. Conversely, FIG. 2 shows that irradiation has a dramatic affect on the percent permanent set performance of the ethylene polymers. However, FIG. 2 (like FIG. 1 and the results shown in WO 95/29197) shows no particular distinction between the various polymers as the polymer density dominated the percent permanent set response and radiation affected the various polymer equally.

Figure 3:
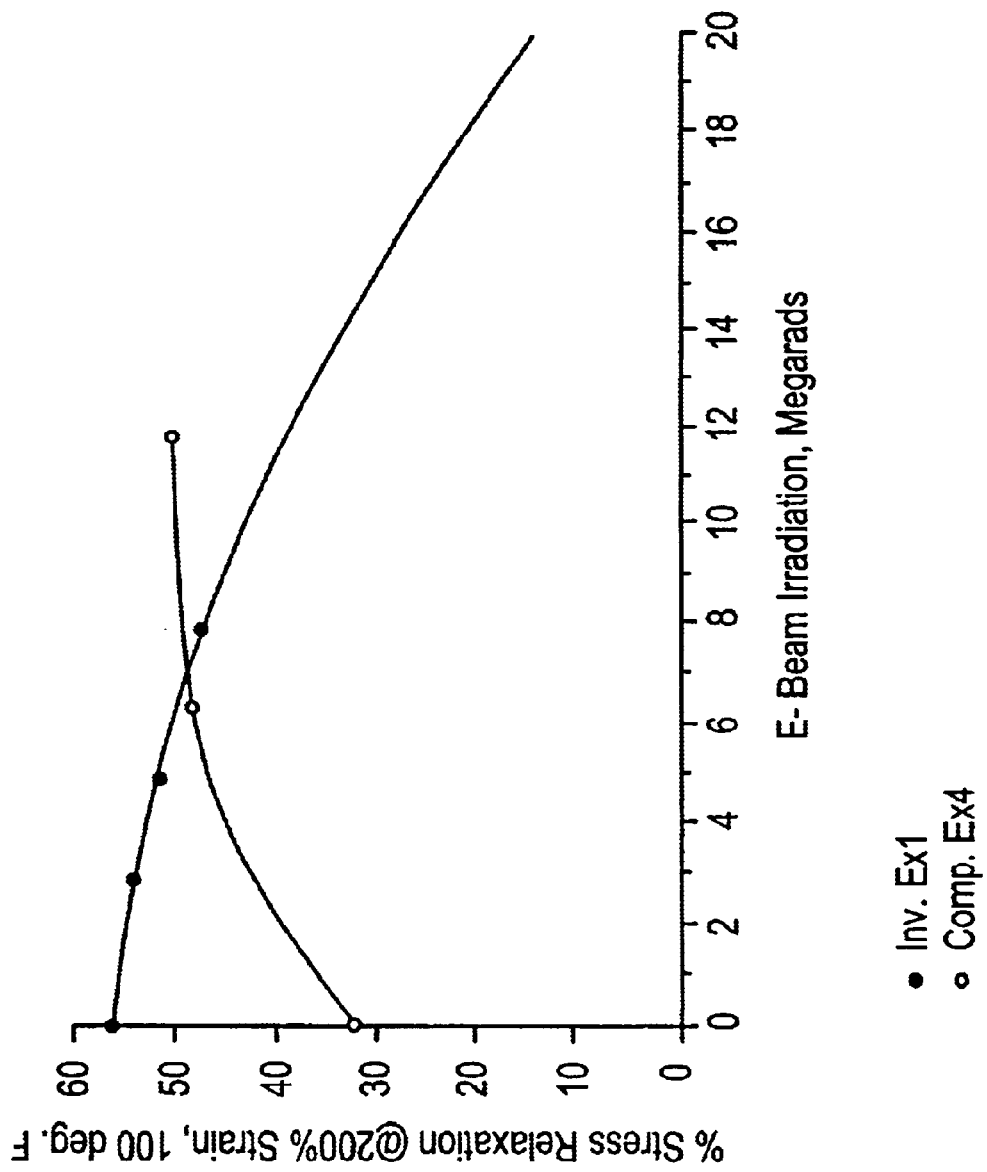
FIG. 3 is a plot of percent stress relaxation at 38° C. versus megarads of electron beam radiation for Inventive Example 1 and comparative run 4.

In another evaluation, 2 mil cast films of Resin A and Resin D were subjected to varying dosages of electron beam radiation and evaluated to determine their respective percent stress or load relaxation performances at 38° C. This test was performed as described above, except the temperature was 38° C. instead of 23° C. and the sample was held at 200% strain for 1 hour instead for 30 seconds. Table 3 shows the results for this evaluation and FIG. 3 plots the results using the average of duplicative samples as well as a four-datapoint average for Resin D at 5 and 8 megarads of electron beam radiation.

TABLE 2

|  | * | Inventive Ex. 1 | | | * | Inventive Ex. 2 | | | Comparative Ex. 3* | | | |
|---|---|---|---|---|---|---|---|---|---|---|---|---|
| Resin | A | A | A | A | B | B | B | B | C | C | C | C |
| e-Beam, megarad | 0 | 3 | 5 | 8 | 0 | 3 | 5 | 8 | 0 | 3 | 5 | 8 |
| 100% Strain Load g/inch | 232 | 242 | 254 | 259 | 191 | 170 | 211 | 214 | 330 | 315 | 318 | 327 |
| 200% Strain Load, g/inch | 269 | 290 | 318 | 354 | 226 | 211 | 235 | 238 | 409 | 384 | 380 | 395 |
| % Strain @ Break | 762 | 651 | 785 | 491 | 1109 | 896 | 973 | 860 | 667 | 676 | 697 | 410 |
| % Permanent Set @ 200% Strain | 21 | 9 | 10 | 22 | 17 | 11 | 7.5 | 6.6 | 41 | 28 | 20 | 23 |
| % Stress Relaxation @ 200% Strain | 19 | 18 | 16 | 19 | 20 | 17 | 19 | 20 | 22 | 20 | 25 | 21 |
| % Xylene Extractive | NA | 98.7 | 91.04 | 68.2 | NA | 99.6 | 99.1 | 99.6 | NA | 99.6 | 99.8 | 73.9 |

|  | Comparative Ex. 4* | | | | Comparative Ex. 5* | | | |
|---|---|---|---|---|---|---|---|---|
| Resin | D | D | D | D | E | E | E | E |
| e-Beam, megarad | 0 | 5 | 8 | 12 | 0 | 5 | 8 | 12 |
| 100% Strain Load g/inch | 331 | 328 | 329 | 397 | 327 | 325 | 303 | 317 |
| 200% Strain Load, g/inch | 387 | 357 | 423 | 379 | 367 | 430 | 382 | 385 |
| % Strain @ Break | 812 | 780 | 883 | 784 | 909 | 869 | 809 | 773 |
| % Permanent Set @ 200% Strain | 42 | 24 | 35 | 22 | 50 | 24 | 24 | 26 |
| % Stress Relaxation @ 200% Strain | 23 | 18 | 23 | 19 | 23 | 23 | 22 | 21 |
| % Xylene Extractive | NA | 99 7 | 99.3 | 81.5 | NA | 99 6 | 99.4 | 77.5 |

*not an example of the invention; provided for comparative purposes only.

TABLE 3

| E-Beam megarads | Maximum Stress, psi | Minimum Stress, psi | % Stress Relaxation |
|---|---|---|---|
| Resin D (Comp. Ex. 4) | | | |
| 0 | 192 | 127 | 33.9 |
| 0 | 181 | 125 | 30.9 |
| 5 | 235 | 112 | 52.3 |
| 5 | 230 | 108 | 53.0 |
| 8 | 231 | 132 | 42.9 |
| 8 | 245 | 136 | 44.5 |
| 12 | 250 | 120 | 52.0 |
| 12 | 227 | 115 | 49.3 |
| Resin A (Inv. Ex. 1) | | | |
| 0 | 126 | 55 | 56.3 |
| 0 | 120 | 53 | 55.8 |
| 3 | 120 | 57 | 52.5 |
| 3 | 134 | 59 | 56.0 |
| 5 | 134 | 64 | 52.2 |
| 5 | 142 | 69 | 51.4 |
| 8 | 137 | 70 | 48.9 |
| 8 | 145 | 78 | 46.2 |

The data in Table 3 and FIG. 3 show surprisingly the irradiation can substantially reduce the elevated temperature percent stress relaxation performance of ethylene interpolymers having densities less than 0.87 g/cm³ and conversely, show irradiation has no effect or increase the elevated temperature stress relaxation performance of ethylene interpolymers characterized as having densities greater than 0.87 g/cm³. The data in Table 3 also show that the minimum stress of ethylene interpolymers characterized as having densities less than 0.87 g/cm³ desirably increases at higher dosage level. Extrapolation of FIG. 3 indicates that at an electron beam radiation dosage level of about 20 megarads, such interpolymer will exhibit a percent stress relaxation at 38° C. of less than 20.

In another evaluation, a homogeneously branched ethylene polymer was evaluated to determine its elongation-tenacity stability upon crosslinking. The homogeneously branched ethylene polymer selected for this evaluation was a substantially linear ethylene/1-octene interpolymer supplied by The Dow Chemical Company under the designation AFFINITY™ EG8200. This interpolymer has 512 melt index and a 0.87 g/cc density. The interpolymer also contained 200 ppm IRGANOX™ 1010, 2000 ppm Chimassorb 944 (both supplied by Ciba-Geigy Corporation) and 800 ppm Standostab PEPQ™ (supplied by Sandox Chemicals). The polymer was meltspun into monofilament fibers of nominal 70–75 denier at Alex-James Corporation and wound onto spools. Subsequently, some of the spools were electron-beam irradiated at 32 Mrad dosage. The stress-strain properties (tenacity and percent elongation) of both crosslinked fibers (Inventive Example 6) and uncrosslinked fibers (comparative run 7) are shown in the FIG. 4.

Figure 4:
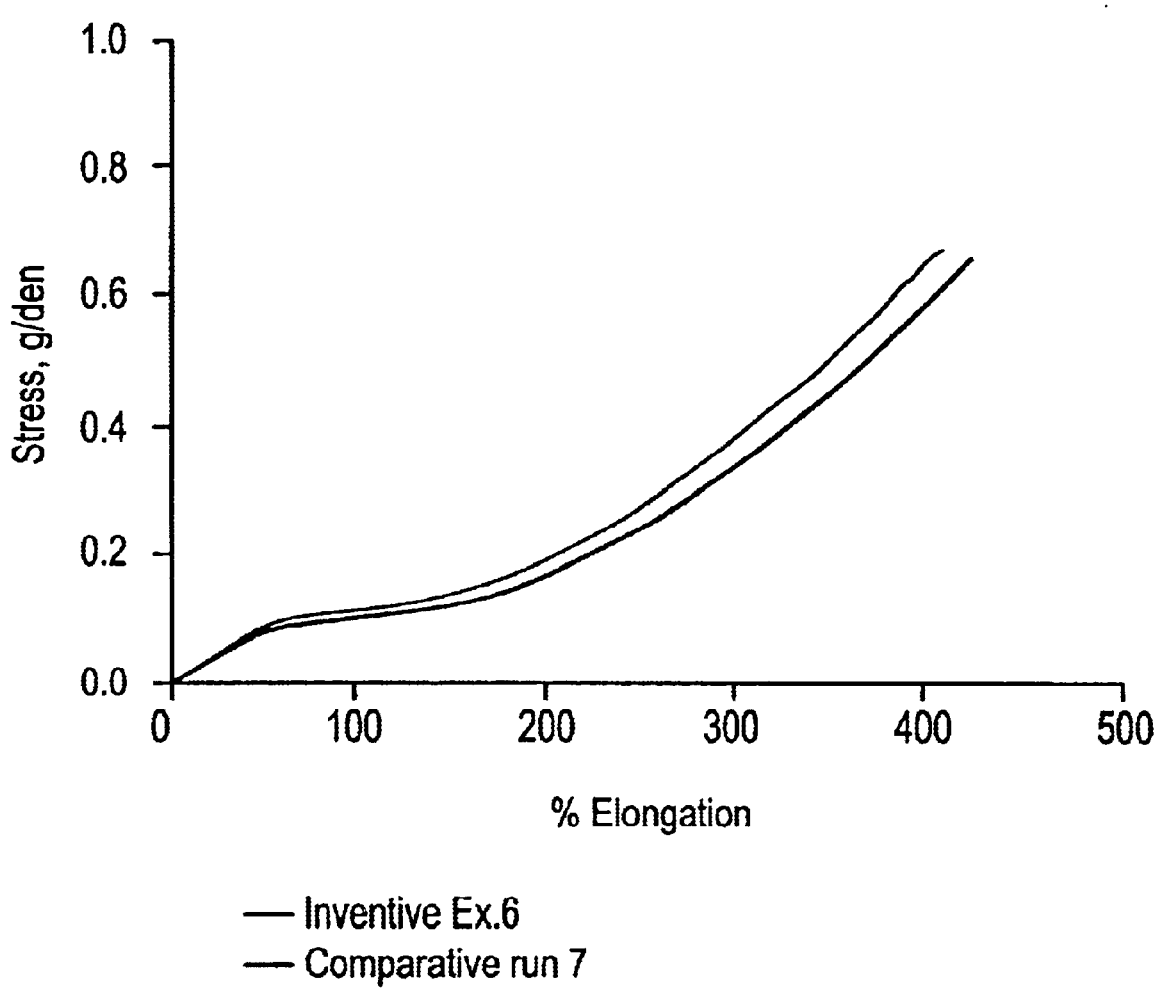
FIG. 4 is a stress-strain comparison between Inventive Example 6 and comparative run 7.

FIG. 4 shows surprisingly the tenacity at break and percent elongation at break for Inventive Example 6 was not substantially reduced as a result of a high degree of crosslinking (about 60–65 percent weight gel content). For the expression $$Abs[\Delta E/E_0] + Abs[\Delta T/T_0]$$

Inventive Example 6 had a value of 0.46.

Figure 5:
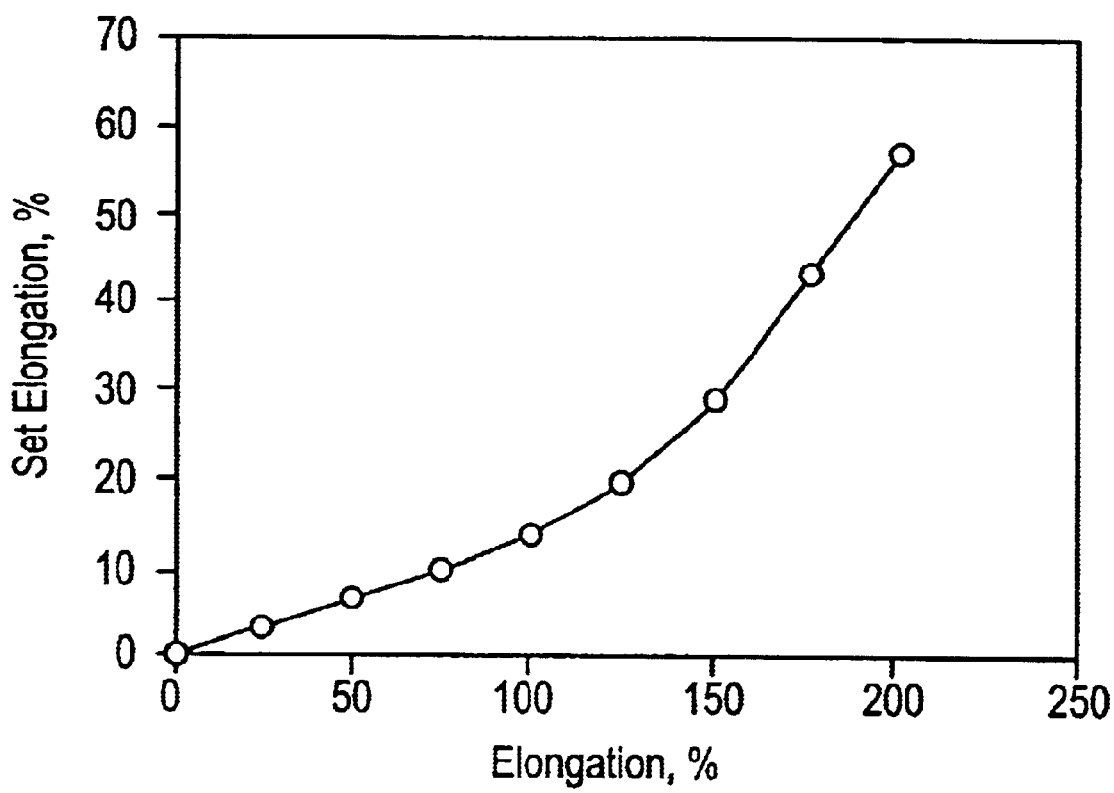
FIG. 5 is a plot of percent elastic recovery (as percent set elongation) versus percent elongation (strain) for Inventive Example 6.

FIG. 5 which shows the elastic recovery (percent permanent set) results for Inventive Example 6 indicates this fiber exhibited adequate elastic recovery at percent elongations less than 100 percent as it would be used in a fabric form.

In another evaluation, the heat resistance of fibers was evaluated by exposing the fibers to elevated temperatures in a strained state. This test determines the survival probability of fibers subject to heat setting and ironing. Because fiber in the fabric is in extended state, this test was conducted with fibers were tested in strained form.

Two strains, 50 percent and 300 percent, were used in the test. The exposure to heat was 1 min, hence the test measures resistance to heat shock. Fibers were stretched to the desired extension in a lab stretcher and exposed to heat by inserting the stretcher in a temperature-equilibrated forced-air oven for 1 minute. The oven temperature was increased at 5° C. increments using new samples for each test until fiber fracture occurred for at least two repeats. The temperature where fracture occurred was recorded for each strain.

In this test, the heat resistance for comparative run 7 fiber was about 80° C. at 50 percent elongation and 70° C. at 300 percent elongation. Conversely, the heat resistance of Inventive Example 6 was dramatically improved. That is, for Inventive Example 6, the heat resistance was greater than 250° C. at both 50 percent and 300 percent elongation.

We claim:

1. A heat-resistant, shaped, irradiated and crosslinked article free of a silane crosslinker, and comprising an ethylene interpolymer of ethylene interpolymerized with at least one other monomer and characterized as having:
   a) an interpolymer density of less than 0.89 g/cm³ or a DSC crystallinity at 23° C., as determined using differential scanning calorimetry, of less than about 26 weight percent before being shaped, irradiated and crosslinked,
   b) xylene extractables of less than or equal to about 70 weight percent and
   wherein the article is in the form of a film.

2. A heat-resistant, shaped and elastic article free of a silane crosslinker and which comprises at least one ethylene interpolymer which has been irradiated and crosslinked wherein the interpolymer comprises ethylene interpolymerized with at least one other monomer and is characterized as having:
   (a) an interpolymer density of less than or equal to 0.89 g/cm³ or a DSC crystallinity at 23° C., as determined using differential scanning calorimetry, of less than about 26 weight percent before being shaped, irradiated and crosslinked,
   (b) a percent permanent set of less than 60 at 23° C. and 200 percent strain when measured at a 2 mil thickness using an Instron tensiometer after being shaped, irradiated and crosslinked,
   (c) a percent stress relaxation of less than or equal 25 at 23° C. and 200 percent strain when measured at a 2 mil thickness using a Instron tensiometer after being shaped, irradiated and crosslinked,
   (d) a percent stress relaxation of less than or equal 55 at 38° C. and 200 percent strain when measured at a 2 mil thickness using an Instron tensiometer after being shaped, irradiated and crosslinked, and
   wherein the article is in the form of a film.

3. A heat-resistant, shaped, irradiated and crosslinked article free of a silane crosslinker, and comprising an ethylene interpolymer of ethylene interpolymerized with at least one other monomer and characterized as having:
   a) an interpolymer density of less than 0.89 g/cm³ or a DSC crystallinity at 23° C., as determined using differential scanning calorimetry, of less than about 26 weight percent before being shaped, irradiated and crosslinked, b) xylene extractables of less than or equal to about 70 weight percent, and wherein the article is in the form of a molding.

4. A heat-resistant, shaped and elastic article free of a silane crosslinker and which comprises at least one ethylene interpolymer which has been irradiated and crosslinked wherein the interpolymer comprises ethylene interpolymerized with at least one other monomer and is characterized as having:

(a) an interpolymer density of less than or equal to 0.89 g/cm$^3$ or a DSC crystallinity at 23° C., as determined using differential scanning calorimetry, of less than about 26 weight percent before being shaped, irradiated and crosslinked, (b) a percent permanent set of less than 60 at 23° C. and 200 percent swain when measured at a 2 mil thickness using an Instron tensiometer after being shaped, irradiated and crosslinked, (c) a percent stress relaxation of less than or equal 25 at 23° C. and 200 percent strain when measured at a 2 mil thickness using a Instron tensiometer after being shaped, irradiated and crosslinked, (d) a percent stress relaxation of less than or equal 55 at 38° C. and 200 percent strain when measured at a 2 mil thickness using an Instron tensiometer alter being shaped, irradiated and crosslinked, and wherein the article is in the form of a molding.

5. A heat-resistant, shaped, irradiated and crosslinked article free of a silane crosslinker, and comprising an ethylene interpolymer of ethylene interpolymerized with at least one other monomer and characterized as having:

a) an interpolymer density of less than 0.89 g/cm$^3$ or a DSC crystallinity at 23° C., as determined using differential scanning calorimetry, of less than about 26 weight percent before being shaped, irradiated and crosslinked, b) xylene extractables of less than or equal to about 70 weight percent, and wherein the article is in the form of a thermoform.

6. A heat-resistant shaped and elastic article free of a silane crosslinker and which comprises at least one ethylene interpolymer which has been irradiated and crosslinked wherein the interpolymer comprises ethylene interpolymerized with at least one other monomer and is characterized as having:

(a) an interpolymer density of less than or equal to 0.89 g/cm$^3$ or a DSC crystallinity at 23° C., as determined using differential scanning calorimetry, of less than about 26 weight percent before being shaped irradiated and crosslinked, (b) a percent permanent set of less than 60 at 23° C. and 200 percent strain when measured at a 2 mil thickness using an Instron tensiometer after being shaped, irradiated and crosslinked, (c) a percent stress relaxation of less than or equal 25 at 23° C. and 200 percent strain when measured at a 2 mil thickness using a Instron tensiometer after being shaped, irradiated and crosslinked, (d) a percent stress relaxation of less than or equal 55 at 38° C. and 200 percent strain when measured at a 2 mil thickness using an Instron tensiometer after being shaped, irradiated and crosslinked, and wherein die article is in the form of a thermoform.

7. A heat-resistant, shaped, irradiated and crosslinked article free of a silane crosslinker, and comprising an ethylene interpolymer of ethylene interpolymerized with at least one other monomer and characterized as having:

a) an interpolymer density of less than 0.89 g/cm$^3$ or a DSC crystallinity at 23° C., as determined using differential scanning calorimetry, of less than about 26 weight percent before being shaped, irradiated and crosslinked, b) xylene extractables of less than or equal to about 70 weight percent and wherein the article is in the form of a personal hygiene item.

8. The item of claim 7 wherein the item is a disposable diaper.

9. The item of claim 8 wherein the diaper comprises a backsheet or a topsheet comprised of the shaped interpolymer.

10. A heat-resistant, shaped and elastic article free of a silane crosslinker and which comprises at least one ethylene interpolymer which has been irradiated and crosslinked wherein the interpolymer comprises ethylene interpolymerized with at least one other monomer and is characterized as having:

(a) an interpolymer density of less than or equal to 0.89 g/cm$^3$ or a DSC crystallinity at 23° C., as determined using differential scanning calorimetry, of less than about 26 weight percent before being shaped, irradiated and crosslinked, (b) a percent permanent set of less than 60 at 23° C. and 200 percent strain when measured at a 2 mil thickness using an matron tensiometer after being shaped, irradiated and crosslinked, (c) a percent stress relaxation of less than or equal 25 at 23° C. and 200 percent strain when measured at a 2 mil thickness using a Instron tensiometer after being shaped, irradiated and crosslinked, (d) a percent stress relaxation of less than or equal 55 at 38° C. and 200 percent stain when measured at a 2 mil thickness using an Instron tensiometer after being shaped, irradiated and crosslinked, and wherein the article is in the form of a personal hygiene item.

11. The item of claim 10 wherein the item is a disposable diaper.

12. The item of claim 11 wherein the diaper comprises a backsheet or a topsheet comprised of the shaped interpolymer.

13. A heat-resistant, shaped, irradiated and crosslinked article free of a silane crosslinker, and comprising an ethylene interpolymer of ethylene interpolymerized with at least one other monomer and characterized as having:

a) an interpolymer density of less than 0.89 g/cm$^3$ or a DSC crystallinity at 23° C., as determined using differential scanning calorimetry, of less than about 26 weight percent before being shaped, irradiated and crosslinked, b) xylene extractables of less than or equal to about 70 weight percent, and wherein the article is in the form of an infection control item.

14. A heat-resistant, shaped and elastic article free of a silane crosslinker and which comprises at least one ethylene interpolymer which has been irradiated and crosslinked wherein the interpolymer comprises ethylene interpolymerized with at least one other monomer and is characterized as having:

(a) an interpolymer density of less than or equal to 0.89 g/cm$^3$ or a DSC crystallinity at 23° C., as determined using differential scanning calorimetry, of less than about 26 weight percent before being shaped, irradiated and crosslinked,
(b) a percent permanent set of less than 60 at 23° C. and 200 percent strain when measured at a 2 mil thickness using an Instron tensiometer after being shaped, irradiated and crosslinked,
(c) a percent stress relaxation of less than or equal 25 at 23° C. and 200 percent strain when measured at a 2 mil thickness using a Instron tensiometer after being shaped, irradiated and crosslinked,
(d) a percent stress relaxation of less than or equal 55 at 38° C. and 200 percent strain when measured at a 2 mil thickness using an Instron tensiometer after being shaped, irradiated and crosslinked, and
wherein the article is in the form of an infection control item.

* * * * *